(12) United States Patent
Fiedler et al.

(10) Patent No.: US 11,560,402 B2
(45) Date of Patent: Jan. 24, 2023

(54) METHOD FOR CLEAVAGE OF SOLID PHASE-BOUND PEPTIDES FROM THE SOLID PHASE

(71) Applicant: SANOFI-AVENTIS DEUTSCHLAND GMBH, Frankfurt am Main (DE)

(72) Inventors: Wolfgang Fiedler, Frankfurt am Main (DE); Norbert Pleuss, Frankfurt am Main (DE); Bernd Henkel, Frankfurt am Main (DE); Manfred Gerken, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 16/380,316

(22) Filed: Apr. 10, 2019

(65) Prior Publication Data

US 2019/0330266 A1 Oct. 31, 2019

(30) Foreign Application Priority Data

Apr. 10, 2018 (EP) .................... 18166546

(51) Int. Cl.
*C07K 1/12* (2006.01)
*C07K 1/04* (2006.01)
*C07K 14/605* (2006.01)

(52) U.S. Cl.
CPC .............. *C07K 1/122* (2013.01); *C07K 1/042* (2013.01); *C07K 14/605* (2013.01)

(58) Field of Classification Search
CPC ............ C07K 1/00; C07K 1/04; C07K 1/003; C07K 1/006; C07K 1/22; C07K 14/605; C07K 1/122; C07K 1/042; A61K 38/26; A61K 38/2278
See application file for complete search history.

(56) References Cited

U.S. PATENT DOCUMENTS

| | | | |
|---|---|---|---|
| 5,424,286 A | 6/1995 | Eng | |
| 6,528,486 B1 | 3/2003 | Larsen | |
| 7,431,685 B2 | 10/2008 | Frey | |
| 2005/0176079 A1 | 8/2005 | Chu | |
| 2008/0019911 A1 | 1/2008 | Xu et al. | |
| 2011/0286982 A1* | 11/2011 | Meier | A61P 3/06 424/93.21 |
| 2013/0289241 A1* | 10/2013 | Bai | C07K 14/57563 530/334 |
| 2015/0291682 A1 | 10/2015 | Vuilleumier | |
| 2015/0322129 A1 | 11/2015 | Bossart | |
| 2017/0313740 A1* | 11/2017 | Wang | C07K 1/04 |
| 2018/0155406 A1 | 6/2018 | Bossart et al. | |
| 2019/0330266 A1 | 10/2019 | Fiedler | |

FOREIGN PATENT DOCUMENTS

| | | | |
|---|---|---|---|
| CN | 101357938 A | * | 2/2009 |
| CN | 103819553 A | | 5/2014 |
| CN | 104 844 706 A | | 8/2015 |
| CN | 104844706 A | | 8/2015 |
| EP | 1076066 A1 | | 2/2001 |
| EP | 1107969 B1 | | 6/2001 |
| JP | H07-097401 | | 4/1995 |
| JP | 2011-510954 | | 4/2011 |
| RU | 2458066 C1 | | 5/2011 |
| WO | WO 1998/005351 A1 | | 2/1998 |
| WO | WO 1998/030231 A1 | | 7/1998 |
| WO | WO 1999/007404 A1 | | 2/1999 |
| WO | WO 1999/025727 A2 | | 5/1999 |
| WO | WO 1999/025728 A1 | | 5/1999 |
| WO | WO 2000/012506 A2 | | 3/2000 |
| WO | WO 2000/012506 A3 | | 6/2000 |
| WO | WO 2001/004156 A1 | | 1/2001 |
| WO | WO 2004/005342 A1 | | 1/2004 |
| WO | WO 2004/035623 A2 | | 4/2004 |
| WO | WO 2007/004675 A1 | | 1/2007 |
| WO | WO 2006/134340 A9 | | 3/2009 |
| WO | WO 2011/012723 A1 | | 7/2009 |
| WO | WO 2010/011439 A2 | | 1/2010 |
| WO | WO 2010/148089 A1 | | 12/2010 |
| WO | WO-2011160630 A2 * | 12/2011 | ............. A61K 45/06 |
| WO | WO 2012/088116 A2 | | 6/2012 |
| WO | WO 2013/192129 A1 | | 12/2013 |
| WO | WO 2013/192130 A1 | | 12/2013 |
| WO | WO 2014/049610 A2 | | 4/2014 |
| WO | WO 2014/056872 A1 | | 4/2014 |
| WO | WO 2014/096145 A1 | | 6/2014 |
| WO | WO 2015/067716 A1 | | 5/2015 |
| WO | WO 2015/086731 A1 | | 6/2015 |
| WO | WO 2015/086732 A1 | | 6/2015 |

(Continued)

OTHER PUBLICATIONS

Palladino et al., "New TFA-Free Cleavage and Final Deprotection in Fmoc Solid-Phase Peptide Synthesis: Dilute HCI in Fluoro Alcohol", Organic Letters, 2012, 6346-6349 (Year: 2012).*
Cambridge Research Biomaterials, "Fmoc Solid-Phase Synthesis", 2020 (Year: 2020).*
Rapp Polymere, "Rink Amide Linker on Aminomethyl Polystyrene Resin", 2017 (Year: 2017).*
Azuma et al. "Dipicolylamine as a unique structural switching element for helical peptides", Organic & Biomolecular Chemistry, 2012, pp. 6062-6068 (Year: 2012).*
ChemPep Inc., "Fmoc Solid Phase Peptide Synthesis", 2007, 11 pages (Year: 2007).*
Kluczyk et al. "Microwave-assisted TFA cleavage of peptides from Merrifield resin", Journal of Peptide Science, 2009, pp. 31-39 (Year: 2009).*

(Continued)

*Primary Examiner* — Lianko G Garyu
(74) *Attorney, Agent, or Firm* — Lathrop GPM LLP; James H. Velema, Esq.

(57) ABSTRACT

The invention relates to a method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature in the range of about 23° C. to about 29° C.

15 Claims, 15 Drawing Sheets

Specification includes a Sequence Listing.

(56) References Cited

FOREIGN PATENT DOCUMENTS

| WO | WO 2015/086733 A1 | 6/2015 |
|---|---|---|
| WO | WO 2015/155141 A1 | 10/2015 |
| WO | WO 2016/198624 A1 | 12/2016 |
| WO | WO 2017/162650 A1 | 9/2017 |
| WO | WO 2018/069295 | 4/2018 |

OTHER PUBLICATIONS

CEM Coroporation Application Note: Peptide Cleavage and Protected Cleavage Producers, 2017, 2 pages (Year: 2017).*
National Center for Biotechnology Information (2022). PubChem Compound Summary for CID 56669849, Exendin 4 (Heloderma suspectum). Retrieved May 6, 2022 from https://pubchem.ncbi.nlm.nih.gov/compound/Exendin-4-_Heloderma-suspectum (Year: 2022).*
Anonymous: "Introduction to Fmoc Solid Phase Peptide Synthesis", Protein Technologies, Inc., Jan. 2006, Document #9040019 Rev. 02 (XP055498187).
E. Atherton et al., Solid phase peptide synthesis, A Practical Approach, Oxford-IRL Press, New York, 1990.
E. Göke et al., "Exendin-4 Is a High Potency Agonist and Truncated Exendin-(9-39)-amide an Antagonist at the Glucagon-like Peptide 1-(7-36)-amide Receptor of Insulin-Secreting Beta Cells", Journal of Biological Chemistry, Sep. 15, 1993, vol. 268, No. 26, pp. 19650-19655.
European Search Report for European Patent Application No. 18166546, dated Oct. 3, 2018, 2 pages.
Extended European Search Report for European Patent Application No. 18166551.4, dated Aug. 16, 2018.
G B Fields et al., "Solid-phase peptide synthesis and solid-state NMR spectroscopy of [Ala$^3$-$^{15}$N][Val$^1$]gramicidin A", Proc. Natl. Acad. Sci. USA, Mar. 1988, vol. 85, No. 5, pp. 1384-1388.
G. Heinrich et al., "Pre-Proglucagon messenger ribonucleic acid: nucleotide and encoded amino acid sequences of the rat pancreatic complementary deoxyribonucleic acid", Endocrinology, 1984, vol. 115, No. 6, pp. 2176-2181.
H. Echner et al., "Eine neue Synthese von Thymosin $\alpha_1$", Liebigs Ann. Chem., Jul. 6, 1988, Issue 11, pp. 1095-1097.
International Search Report and Written Opinion for PCT International Patent Application No. PCT/EP2019/059090, dated May 2, 2019.
J. Eng et al., "Isolation and characterization of exendin-4, an exendin-3 analogue, from Heloderma suspectum venom", The Journal of Biological Chemistry, Apr. 15, 1992, vol. 267, No. 11, pp. 7402-7405.
J. Holst, "Glucagon-like Peptide-1, a Gastrointestinal Hormone with a Pharmaceutical Potential", Current Medicinal Chemistry, 1999, vol. 6, No. 11, pp. 1005-1017, PMID:10519910.
J. Houben et al., Methods in Organic Chemistry, vol. E22a, Synthesis of Peptides and Peptidomimetics, M. Goodman, A. Felix, L. Moroder, C. Toniolo, (Eds.), Thieme Verlag, Stuttgart, New York, 2002.
J. Jones, The Chemical Synthesis of Peptides, New York, Oxford University Press, 1991.
J. Raufman, "Bioactive peptides from lizard venoms", Regulatory Peptides, 1996, vol. 61, pp. 1-18, PMID 8701022.
King et al., "A cleavage method which minimizes side reactions following Fmoc solid phase peptide synthesis", International Journal of Peptide & Protein Research, Sep. 1990, vol. 36, No. 3, pp. 255-266.
L. O. Uttenthal et al., "Molecular forms of glucagon-like peptide-1 in human pancreas and glucagonomas", Journal of Clinical Endocrinology and Metabolism, 1985, vol. 61, No. 3, pp. 472-479, PMID 2991321.

Liang et al. "Tumor-specific penetrating peptides-functionalized hyaluronic acid-d-α-tocopheryl succinate based nanoparticles for multi-task delivery to invasive cancers", Biomaterials 2015, vol. 71, pp. 11-23.
M. A. Nauck et al., "Glucagon-like peptide 1 (GLP-1) as a new therapeutic approach for type 2-diabetes", Exp. Clin. Endocrinol Diabetes, 1997, vol. 105 No. 4, pp. 187-195.
M. Lopez-Delgado et al., "Effects of glucagon-like peptide 1 on the kinetics of glycogen synthase α in hepatocytes from normal and diabetic rats", Endocrinology, 1998, vol. 139, No. 6, pp. 2811-2817, PMID 9285204.
M. Pennington et al., Peptide Synthesis Protocols, Humana Press, Totowa, New Jersey, 1995.
P. Sieber, "Modification of Tryptophan Residues During Acidolysis of 4-Methoxy-2, 3, 6-Trimethylbenzenesulfonyl Groups. Effects of Scavengers", Tetrahedron Letters, vol. 28, No. 15, 1987, pp. 1637-1640.
R. Eritja et al., "On the use of S-t-butylsulphenyl group for protection of cysteine in solid-phase peptide synthesis using FMOC-amino acids", Tetrahedron, 1987, vol. 43, No. 12, pp. 2675-2680.
Xiaoyu et al., "Recent Developments in the Research of Exendin-4 and Its Analogs", Progress in Pharmaceutical Sciences, 2007,vol. 31, No. 9, pp. 403-407.
Xu et al., "Recent Advances in Radionuclide-Labeled Analogues of Exendin-4 for Insulinoma Imaging", Cancer Res Prev Treat, 2013. vol. 42, No. 4, 20 pages.
International Search Report in related PCT Application No. PCT/EP2019/059083, dated Jun. 14, 2019 (4 pages).
Bhat et al., "A DPP-IV-resistant triple-acting agonist of GIP, GLP-1 and glucagon receptors with potent glucose-lowering and insulinotropic actions in high-fat-fed mice" Diabetologia. Jun. 2013;56(6):1417-24.
Bhat et al., "A novel GIP-oxyntomodulin hybrid peptide acting through GIP, glucagon and GLP-1 receptors exhibits weight reducing and anti-diabetic properties" Biochem Pharmacol. Jun. 1, 2013;85(11):1655-62.
Biancalana et al., "Molecular mechanism of Thioflavin-T binding to amyloid fibrils" Biochim Biophys Acta. Jul. 2010;1804(7):1405-12.
Druce et al., "Investigation of structure-activity relationships of Oxyntomodulin (Oxm) using Oxm analogs" Endocrinology. Apr. 2009;150(4):1712-22.
Finan et al., "A rationally designed monomeric peptide triagonist corrects obesity and diabetes in rodents" Nat Med. Jan. 2015;21(1):27-36.
Hargrove et al., "Biological activity of AC3174, a peptide analog of exendin-4" Regul Pept. Jun. 7, 2007;141(1-3):113-9.
Heppner et al., "Glucagon regulation of energy metabolism" Physiol Behav. Jul. 14, 2010;100(5):545-8.
International Search Report for PCT/EP2017/081125, dated Feb. 3, 2018.
International Search Report for PCT/EP2017/081126, dated Feb. 3, 2018.
Kaiser et al., "Color test for detection of free terminal amino groups in the solid-phase synthesis of peptides" Anal Biochem. Apr. 1970;34(2):595-8.
Krstenansky et al., "Importance of the 10-13 region of glucagon for its receptor interactions and activation of adenylate cyclase" Biochemistry. Jul. 1, 1986;25(13):3833-9.
Naiki et al., "Fluorometric determination of amyloid fibrils in vitro using the fluorescent dye, thioflavin T1", Anal Biochem. Mar. 1989;177(2):244-9.
Pocai, "Action and therapeutic potential of oxyntomodulin", Mol Metab. Dec. 14, 2013;3(3):241-51.
Vojkovsky, "Detection of secondary amines on solid phase" Pept Res. Jul.-Aug. 1995;8(4):236-7.
Vilà et al., "A convenient solid-phase strategy for the synthesis of anti-microbial cyclic lipopeptides", Organic & Biomolecular Chemistry, 2013,11: 3365-3374.
Jakubke, Amino acids, peptides and proteins, 1985, pp. 189-191.

* cited by examiner

Figure 2

SEQ ID NO: 1 AVE0010 (44 AS)

H-G-E-G-T-F-T-S-D-L-S-K-Q-M-E-E-E-A-V-R-L-F-I-E-W-L-K-N-G-G-P-S-S-G-A-P-P-S-K-K-K-K-K-K-NH$_2$

SEQ ID NO: 2 Exendin-4 (39 AS)

H-G-E-G-T-F-T-S-D-L-S-K-Q-M-E-E-E-A-V-R-L-F-I-E-W-L-K-N-G-G-P-S-S-G-A-P-P-P-S-NH$_2$

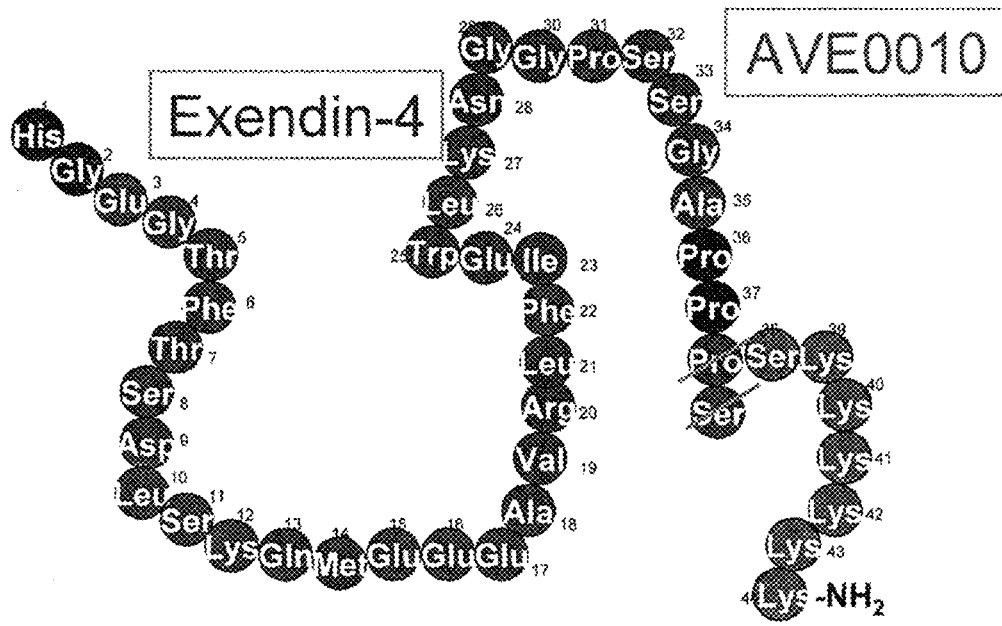

SEQ ID NO:3: Exendin-3 (J. Bio. Chem., 267, 1992, 7402-7405)

H-His-Ser-Asp-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$)

SEQ ID NO: 4: GLP-1 (7-36) amide

H-A-E-G-T-F-T-S-D-V-S-S-Y-L-E-G-Q-A-A-K-E-F-I-A-W-L-V-K-G-R-NH$_2$

1 Fmoc(22-44)+Arg
2 (22-44)+Arg
3 Ac(22-44)+Arg
4 Fmoc(22-44)+Arg+Val

METHOD FOR CLEAVAGE OF SOLID PHASE-BOUND PEPTIDES FROM THE SOLID PHASE

RELATED APPLICATIONS

This application claims the benefit of European Patent Application No. 18166546.4, filed Apr. 10, 2018, the entire disclosure of which is hereby incorporated herein by reference in its entirety.

DESCRIPTION

The present invention relates to a method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature in the range of about 23° C. to 29° C.

The invention further relates to a composition, consisting essentially of trifluoroacetic acid and 1,2-ethanedithiol, wherein the composition comprises trifluoroacetic acid in an amount of 95 to 99% v/v, and 1,2-ethanedithiol in an amount of 1 to 5% v/v.

The invention further relates to the use of a composition, consisting essentially of trifluoroacetic acid and 1,2-ethanedithiol, wherein the composition comprises trifluoroacetic acid in an amount of 95 to 99% v/v, and 1,2-ethanedithiol in an amount of 1 to 5% v/v, for cleavage of a peptide bound to a solid phase, from the solid phase.

Established methods of solid phase peptide synthesis teach coupling of the pre-determined C-terminal amino acid of the amino acid chain to be synthesized to a polymer carrier via a linker. The amino acid used for coupling is an amino acid building block having an N-terminally protected amino group, said protective group being a temporarily linked Fmoc group. After successful coupling, the Fmoc protective group is cleaved and the next Fmoc-protected amino acid building block is coupled with the free amino function of the previous amino acid building block. When the desired amino acid chain is synthesized, it is cleaved from the solid phase. FIG. 1 is giving an overview of the described approach.

The solid phase synthesis of lixisenatide (also known as AVE0010 or ZP-10) described in WO 01/04156 A1, which is enclosed herein by reference, comprises coupling of the individual Fmoc-protected amino acid building blocks in each the same way.

Lixisenatide has the sequence desPro$^{36}$exendin-4(1-39)-Lys$_6$-NH$_2$. This substance is disclosed in WO 01/04156, SEQ ID NO:93 (cf. SEQ ID NO:1 and FIG. 2 of the present application). Exendins are a group of peptides which can lower the blood glucose concentration. Exendins have a certain similarity to the sequence of GLP-1(7-36) (53%, Göke et al., J. Biol. Chem. 268, 19650-55). Exendin-3 and exendin-4 stimulate an increasing cellular cAMP production in pancreatic acinar cells of guinea pigs by interaction with the exendin receptors (Raufman, 1996, Reg. Peptides 61:1-18). In contrast to exendin-4, exendin-3 effects an increase of amylase release in pancreatic acinar cells. Exendins act as GLP-1 antagonists.

Glucagon-like peptide 1 (GLP-1) is an endocrine hormone which enhances the insulin response after oral uptake of glucose or fat. GLP-1 generally lowers the glucagon concentrations, slows down gastric emptying, stimulates the (pro-)insulin biosynthesis, increases the sensibility to insulin and stimulates the insulin-independent glycogen biosynthesis (Holst (1999), Curr. Med. Chem. 6:1005, Nauck et al. (1997), Exp. Clin. Endocrinol. Diabetes 105:187, Lopez-Delgado et al. (1998), Endocrinology 139:2811). Human GLP-1 has 37 amino acid residues (Heinrich et al., Endocrinol. 115:2176 (1984), Uttenthal et al., J. Clin. Endocrinol. Metabol. (1985), 61:472). Active fragments of GLP-1 include GLP-1(7-36) and GLP-1(7-37).

It was suggested that exendin-3, exendin-4 and exendin agonists can be used for the treatment of diabetes mellitus and the prevention of hyperglycemia, as they reduce gastric emptying and motility (U.S. Pat. No. 5,424,286 and WO 98/0535 A1).

Exendin analogues may be characterized by amino acid substitutions and/or C-terminal truncations of the native exendin-4 sequence. Such exendin analogues are described in WO 99/07404, WO 99/25727 and WO 99/25728.

Cleavage of a peptide synthesized on a solid phase, in particular on a resin, is a complex chemical reaction. On the one hand, the peptide must be cleaved from the solid phase. On the other hand, protection groups, being present on the side chains of the amino acid building blocks, can be removed. The protection groups and the protection group fragments, now present in the liquid phase, are inactivated by so-called "scavengers", as they still can react with the peptide to form undesired by-products.

Solid phase-bound peptides, being produced with Fmoc-protected amino acid building blocks, can be cleaved from the solid phase by trifluoroacetic acid (TFA). Furthermore, TFA removes acid-labile protecting groups, which can be present at the side chains of the amino acid building blocks.

Prior art methods for cleavage of solid-phase bound peptides employ a composition containing TFA and a number of scavengers, for example 3, 4 or 5 scavengers, to remove highly reactive species, occurring after cleavage of the protecting groups from the side chains, and which could covalently modify the amino acid residues in the peptide. King et al. (Int. J. Peptide Proteine Res: 36, 1990, 255-266) disclose a comparison of "Reagent K" (82.5% TFA, 5% phenol, 5% H$_2$O, 5% thioanisole, 2.5% 1,2-ethanedithiol) with compositions of TFA with 2-4 different scavengers. "Reagent K" was found to be most effective in cleavage and inhibition of undesired side reactions in 10 different peptides, each containing 20-50 amino acid residues and being produced with a Fmoc-based solid phase synthesis method. Tests were performed at room temperature.

If cleavage from the solid phase is incomplete, or the protecting groups of the side chain are not completely removed, the cleavage reaction can be repeated. Such additional cleavage is termed herein "second cleavage" or "subsequent cleavage".

The problem of the invention is the improvement of the peptide yield in the solid phase synthesis of a peptide, in particular a GLP-1 agonist. If coupling of the amino acid building blocks to the solid phase-bound amino acid chain is completed, the amino acid chain is cleaved from the solid phase. The solid phase, containing the peptide, is contacted with a cleavage reagent, wherein the peptide, in particular the GLP-1 agonist, is cleaved from the solid phase, and protection groups, optionally present on the amino acid side chains, are removed.

The inventors have found that the reaction temperature and the components of the cleavage reagent significantly influence the yield of the peptide. In view of the prior art cleavage methods, the cleavage method of the present invention is characterized by 1. increase of the reaction temperature beyond the room temperature,
2. reduction of the number of components in the cleavage reagent or cleavage composition, or/and
3. optionally, omission of the "second cleavage".

The inventors found that by the method of the invention for cleavage of a solid-phase bound peptide (in particular a GLP-1 agonist) from the solid phase, the yield of the peptide (the raw peptide) can be increased by 5%, resulting in a cost reduction and an increase of production capacity. Furthermore, the impurity profile was not significantly changed.

By the reduction of the number of components in the cleavage cocktail (in view of five components in the comparative King's cocktail), analytic quality control is improved, costs are reduced and handling during the production process is facilitated.

Omission of the second cleavage step leads to a cost reduction, and handling during the production process is facilitated. The amounts of TFA are reduced, so that removal of TFA is facilitated.

A first aspect of the present invention is a method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature in the range of about 23° C. to about 29° C.

Methods for solid-phase synthesis are known by the person skilled in the art. In a preferred aspect, the coupling cycles are performed from the C-terminus to the N-terminus of the sequence to be synthesized. Reaction conditions applied in a solid phase peptide synthesis from the C-terminus to the N-terminus by amino acid building blocks are known by the person skilled in the art. Amino acid building blocks suitable for solid phase synthesis are described herein. In particular, the N-terminal amino group of the amino acid building block is protected by base-labile protecting group, such as Fmoc. FIG. 1 shows synthesis with Fmoc-protected amino acid building blocks.

The solid phase synthesis of lixisenatide (also known as AVE0010 or ZP-10) described in WO 01/04156 A1, which is enclosed herein by reference, comprises coupling of the individual Fmoc-protected amino acid building blocks in each the same way.

All kinds of solid phases suitable for the solid phase synthesis of peptides can be used. In particular, a solid phase comprising a resin can be used. The resin can be a Rink resin (Rink amide resin) or a Tentagel® resin. In a preferred aspect, the solid phase resin is a Rink resin or Rink amide resin.

In particular, the polypeptide is bound to the resin, in particular the Rink amide resin, by a linker. Suitable linkers are known to the skilled person. In the present invention, the term "about" or "approximately" means a range of ±10%, ±5% or ±1%.

In the present invention "consisting essentially of trifluoroacetic acid and 1,2-ethanedithiol" means in particular that additional compounds can be present in the composition in small amounts. In particular, trifluoroacetic acid and 1,2-ethanedithiol are used in the method of the invention in a common degree of purity. Thus, the composition of the invention, consisting essentially of trifluoroacetic acid and 1,2-ethanedithiol, can contain impurities which are commonly present in trifluoroacetic acid and 1,2-ethanedithiol. Percentages of the trifluoroacetic acid and 1,2-ethanedithiol in the composition of the invention or in the method of the invention are 100% together, including impurities which may be present in the trifluoroacetic acid or/and 1,2-ethanedithiol.

In the present invention, "in small amounts" means in particular that additional compounds, such as impurities of the trifluoroacetic acid or/and 1,2-ethanedithiol, can be present in the composition of the invention or in the reaction mixture used in the method of the invention, in an amount of up to 1% v/v, up to 0.5% v/v, up to 0.2% v/v, up to 0.1% v/v, up to 0.05% v/v, or up to 0.02% v/v. If impurities are present which can be solids, the percentage is expressed as w/v.

In the method of the invention, the cleavage composition comprises trifluoroacetic acid in particular in an amount of about 95 to about 99% v/v.

Preferably, the cleavage composition comprises trifluoroacetic acid in an amount of about 96 to about 98% v/v, or in an amount of about 97 to about 99% v/v.

More particular, the composition comprises trifluoroacetic acid in an amount of about 97% v/v.

In the method of the invention, the cleavage composition comprises 1,2-ethanedithiol in particular in an amount of about 1 to about 5% v/v, Preferably, the cleavage composition comprises 1,2-ethanedithiol in an amount of about 2 to about 4% v/v, or in an amount of about 1 to about 3% v/v.

More particular, the composition comprises 1,2-ethanedithiol in an amount of about 3% v/v.

In the method of the invention, a preferred cleavage composition essentially consists of trifluoroacetic acid in an amount of about 96 to about 98% v/v, and the balance is 1,2-ethanedithiol in an amount of about 4 to about 2% v/v.

In the method of the invention, a preferred cleavage composition essentially consists of trifluoroacetic acid in an amount of about 97 to about 99% v/v, and the balance is 1,2-ethanedithiol in an amount of about 3 to about 1% v/v.

In the method of the invention, another preferred cleavage composition essentially consists of trifluoroacetic acid in an amount of about 96.5 to about 97.5% v/v, and the balance is 1,2-ethanedithiol in an amount of about 3.5 to about 2.5% v/v.

In the method of the invention, another preferred composition essentially consists of trifluoroacetic acid in an amount of about 97% v/v, and 1,2-ethanedithiol in an amount of about 3% v/v.

In the method of the invention as described herein, another preferred composition essentially consists of trifluoroacetic acid and 1,2-ethanedithiol in ratio of 8.25:0.25 (v:v).

The composition of the invention can be a liquid composition. In the method of the invention, the composition can be used in an amount of about 5 to 12 ml/g of peptide on solid phase, in particular 7 to 9 ml/g of peptide on solid phase, or about 8.5 ml/g of peptide on solid phase. The weight of "peptide on solid phase" or "peptide on resin" means the weight of the peptide plus the weight of the solid phase or the resin, to be contacted with the composition of the invention.

More particular, 8.25 ml of TFA/g peptide on solid phase and about 0.25 ml of 1,2-ethanedithiol/g peptide on solid phase can be used in the method of the invention.

In the present invention, it was surprisingly found that cleavage of the peptide from the resin at a temperature larger than room temperature results in an increased yield of the peptide, in particular the GLP-1 agonist.

In the method of the invention, the composition is contacted with the solid phase to which the polypeptide is bound in particular at a temperature of about 25° C. to about 27° C., or at a temperature of about 26° C. to about 29° C., more particular at a temperature of about 25.5° C. to about 26.5° C., most particular at a temperature of about 26° C.

Preferably, the solid phase is contacted with a composition essentially consisting of trifluoroacetic acid in an amount of about 97% v/v, and 1,2-ethanedithiol in an amount of about 3% v/v, at a temperature of about 25° C. to about 27° C.

Also preferred is in the present invention that the solid phase is contacted with a composition essentially consisting of trifluoroacetic acid in an amount of about 97% v/v, and 1,2-ethanedithiol in an amount of about 3% v/v, at a temperature of about 26° C. to about 29° C.

More preferably, the solid phase is contacted with a composition essentially consisting of trifluoroacetic acid in an amount of about 97% v/v, and 1,2-ethanedithiol in an amount of about 3% v/v, at a temperature of about 25.5° C. to about 26.5° C., preferably of about 26° C.

In the method of the invention, the composition is contacted with the solid phase to which the polypeptide is bound for 1 to 8 h, more particular for 4 to 8 h. It is preferred to contact the composition with the solid phase to which the polypeptide is bound for about 4 h, about 5 h, for about 6 h, about 7, or about 8 h.

It is most preferred in the method of the invention to contact the composition with the solid phase to which the polypeptide is bound for 3 to 5 h, in particular for 4 h.

More preferably, the solid phase is contacted with a composition essentially consisting of trifluoroacetic acid in an amount of about 97% v/v, and 1,2-ethanedithiol in an amount of about 3% v/v, at a temperature of about 25.5° C. to about 26.5° C. for about 4 h, preferably of about 26° C., for about 4 h.

In yet another aspect of the invention, no second or subsequent cleavage is performed. In this aspect, in solid phase synthesis of a polypeptide, cleavage according to the method of the invention is performed in a single step.

An amino acid building block according to the invention is a compound which is prolonging the amino acid chain to be synthesized by one or more amino acids in one cycle of the peptide synthesis. In a preferred aspect, an amino acid building block according to the invention prolongs the amino acid chain to be synthesized by 1, 2, 3, or 4 amino acids. In a particularly preferred aspect, the amino acid building block according to the invention prolongs the amino acid chain to be synthesized by one or two amino acids.

The amino acid building block according to the invention preferably comprises one amino acid (mono amino acid building block) or an oligopeptide comprising 2, 3, 4 or more amino acids. In a preferred aspect, the amino acid building block according to the invention comprises one amino acid or a peptide, comprising two amino acids such as e.g. Pro-Pro or His-Gly. Amino acids of an amino acid building block comprising more than one amino acid are preferably linked by peptide bonds. Particularly preferred amino acid building blocks comprising two amino acids are Fmoc-Pro-Pro-OH and Fmoc-His(Trt)-Gly-OH.

It was found that using Fmoc-His(Trt)-Gly-OH instead of amino acid building blocks for His and Gly at positions 1 and 2 in the synthesis of lixisenatide and exendin-4 enables the prevention of undesired DesGly(2)-lixisenatide. Moreover, the obtained lixisenatide did not show enhanced values of D-His resulting from racemization.

Fmoc-His(Trt)-Gly-OH can e.g. be formed by a method comprising the steps of:

i) reacting Fmoc-His(Trt)-OH and H-Gly-OBzl tosylate, and ii) cleaving the benzyl group of the product obtained in step i) to obtain Fmoc-His(Trt)-Gly-OH.

Exemplary reaction conditions are set forth in example 3.

The amino acid building blocks according to the invention can comprise suitable modifications in order to selectively prolong the amino acid chain at the desired positions only. Modifications of the amino acid building block can be performed at the N-terminus, at the C-terminus and/or at the side chains of the amino acids.

To protect the N-terminal amino function of the amino acid building block (i.e. the amino group which is, after successful coupling, the N-terminus of the amino chain), all kinds of protective groups commonly used for the synthesis of peptides, especially for the solid phase synthesis of polypeptides, can be used. The person skilled in the art knows those kinds of suitable temporary protective groups. In a preferred aspect, protective groups which are unstable in alkaline environment can be used. In a preferred aspect the N-terminal amino group of the amino acid building block is protected by an Fmoc-protective group.

The C-terminal carboxy group of the amino acid building block preferably remains unprotected.

The amino acid building block according to the invention can comprise, independently from one another, D-amino acids and glycine, L-amino acids and glycine and/or combinations thereof. In a preferred aspect the amino acids of the amino acid building block according to the invention are selected independently from one another from L-amino acids and glycine. In a preferred aspect, the amino acids can be selected from α-amino acids. In a further aspect the amino acids can be selected from naturally occurring amino acids such as amino acids naturally occurring in polypeptides. In another aspect the amino acid building block according to the invention can comprise artificial amino acids such as Met(O) (methionine sulfoxide or methionine sulfone), Trp(O$_2$) (N-formylkynurenine) and/or isoAsp (β-aspartate or isoaspartate). In a still further preferred aspect the amino acids are selected from Ser, Thr, Trp, Lys, Ala, Asn, Asp, Val, Met, Phe, Ile, Pro, Arg, Glu, Gln, Leu, in particular each in the D-form or each in the L-form, and Gly. In a particularly preferred aspect the amino acid building block according to the invention comprises amino acids selected from Arg, Glu, Gln, Leu, in particular each in the D-form or each in the L-form, and Gly.

In particular the amino acids are selected independently from each other, for example independently from Ser, Thr, Trp, Lys, Ala, Asn, Asp, Val, Met, Phe, Ile, Pro, Arg, Glu, Gln, Leu, in particular each in the D-form or each in the L-form, and Gly.

In one aspect, at least one side chain of the amino acid building block according to the invention can be protected by a further protective group. The further protective group is preferably orthogonal to the N-terminal protective group. Suitable protective groups for said side chains are known by the person skilled in the art. Examples for suitable protective groups are e.g. Trt, Boc, Bzl, Pdf, tBu and OtBu, which can be used for the protection of specific side chains. The person skilled in the art is aware of which side chain needs to be protected by which kind of protective group. In one aspect, amino acid building blocks as mentioned in Example 1.4 can be used. In case the amino acid building block comprises more than one side chain, one or more of these side chains can be protected by protective groups, independently selected from suitable protective groups as known by the person skilled in the art.

The polypeptide to be synthesized may be each possible peptide with a pre-determined sequence. In a preferred aspect, the polypeptide to be synthesized is a GLP-1 agonist. The polypeptide can be a GLP-1 agonist, wherein the GLP-1 agonist is selected from the group consisting of GLP-1 and analogues and derivatives thereof, exendin-3 and analogues and derivatives thereof, exendin-4 and analogues and derivatives thereof. In a preferred aspect the polypeptide is selected from the group consisting of exendin-4 and lixisenatide. A most preferred peptide is lixisenatide. In a further preferred aspect the polypeptide is selected from albiglutide, dulaglutide and semaglutide.

Exendin-3, analogues and derivatives of exendin-3, exendin-4 and analogues and derivatives of exendin-4 are described in WO 01/04156, WO 98/30231, U.S. Pat. No. 5,424,286, EP 99610043.4 and WO 2004/005342. These documents are incorporated herein by reference. Exendin-3, exendin-4 and the analogues and derivatives thereof described in these documents can be synthesized by the method according to the invention, whereas additional modifications can be performed after completion of the synthesis.

Lixisenatide (SEQ ID NO:1, FIG. 2), exendin-4 (SEQ ID NO:2, FIG. 2) and exendin-3 (SEQ ID NO:3, FIG. 2) have a high degree of sequence identity. Sequences of lixisenatide and exendin-4 are identical at positions 1-37. Sequence 1-39 of exendin-4 is identical to exendin-3 at 37 of 39 positions (94%) (J. Biol. Chem. 267, 1992, 7402-7405). Sequence positions are given herein with respect to the sequence of lixisenatide or exendin-4. Starting from these sequences, the person skilled in the art can readily determine corresponding positions in other sequences.

Analogues and derivatives of exendin-3 and/or exendin-4 particularly comprise a modified amino acid sequence. In one aspect, the amino acid sequence is modified by deletion of one or more amino acids (e.g. desPro$^{36}$, desPro$^{37}$, desAsp$^{28}$, desMet(O)$^{14}$) in exendin-4 and the respective positions in exendin-3). In one aspect, one or more amino acids can be replaced (e.g. Met(O)$^{14}$, Trp(O$_2$)$^{25}$, isoAsp$^{28}$, Asp$^{28}$, Pro$^{38}$ in exendin-4 and the respective positions in exendin-3), wherein naturally occurring or artificial amino acids such as e.g. Met(O) (methionine sulfoxide or methionine sulfone), Trp(O$_2$) (N-formylkynurenine) and/or isoAsp (β-aspartate or isoaspartate) can be introduced. Artificial amino acids can readily be introduced in the sequence by using the respective amino acid building blocks in the synthesis cycle.

In one aspect the C-terminus and/or the N-terminus of the polypeptide can be modified, e.g. by the addition of sequences such as -(Lys)-, -(Lys)$_2$-, -(Lys)$_3$-, -(Lys)$_4$-, -(Lys)$_5$-, -(Lys)$_6$-, and -Asn-(Glu)$_5$-. In a preferred aspect, additional amino acid sequences are e.g. -(Lys)$_4$-, -(Lys)$_5$-, -(Lys)$_6$- and -Asn-(Glu)$_5$-. The C-terminal carboxy group is preferably an acid amine group (—NH$_2$). Optionally, the modification of the C-terminus and/or the N-terminus is performed in a separate step after completion of the synthesis cycles of the method according to the invention.

After completion of the synthesis cycles of the method according to the invention, pharmaceutically acceptable salts of the synthesized polypeptides can optionally be formed in an additional step. Methods for the formation of pharmaceutically acceptable salts of polypeptides are known by the person skilled in the art. Preferred pharmaceutically acceptable salts are e.g. acetate salts.

A further preferred GLP-1 agonist is an analogue of exendin-4 selected from the group consisting of:
H-desPro$^{36}$-exendin-4-Lys$_6$-NH$_2$,
H-des(Pro$^{36,37}$)-exendin-4-Lys$_4$-NH$_2$,
H-des(Pro$^{36,37}$)-exendin-4-Lys$_5$-NH$_2$, and pharmaceutically acceptable salts thereof.

A further preferred GLP-1 agonist is an analogue of exendin-4 selected from the group consisting of
desPro$^{36}$[Asp$^{28}$]exendin-4 (1-39),
desPro$^{36}$[IsoAsp$^{28}$]exendin-4 (1-39),
desPro$^{36}$[Met(O)$^{14}$,Asp$^{28}$]exendin-4 (1-39),
desPro$^{36}$[Met(O)$^{14}$,IsoAsp$^{28}$]exendin-4 (1-39),
desPro$^{36}$[Trp(O$_2$)$^{26}$,Asp$^{28}$]exendin-2 (1-39),
desPro$^{36}$[Trp(O$_2$)$^{26}$,IsoAsp$^{28}$]exendin-2 (1-39),
desPro$^{36}$[Met(O)$^{14}$Trp(O$_2$)$^{26}$,Asp$^{28}$]exendin-4 (1-39),
desPro$^{36}$[Met(O)$^{14}$Trp(O$_2$)$^{26}$,IsoAsp$^{28}$]exendin-4(1-39),
and pharmaceutically acceptable salts thereof.

A further preferred GLP-1 agonist is an analogue of exendin-4 selected from the groups as described above, further modified with a -Lys$_6$-NH$_2$ peptide at the C-terminus.

A further preferred GLP-1 agonist is an analogue of exendin-4 selected from the group consisting of:
H-(Lys)$_6$-desPro$^{36}$[Asp$^{28}$]exendin-4(1-39)-Lys$_6$-NH$_2$,
desAsp$^{28}$Pro$^{36}$,Pro$^{37}$,Pro$^{38}$exendin-4(1-39)-NH$_2$,
H-(Lys)$_6$-desPro$^{36}$,Pro$^{37}$,Pro$^{38}$[Asp$^{28}$]exendin-4(1-39)-NH$_2$,
H-Asn-(Glu)$_5$desPro$^{36}$,Pro$^{37}$,Pro$^{38}$[Asp$^{28}$]exendin-4(1-39)-NH$_2$,
desPro$^{36}$,Pro$^{37}$,Pro$^{38}$[Asp$^{28}$]exendin-4(1-39)-(Lys)$_6$-NH$_2$,
H-(Lys)$_6$-desPro$^{36}$,Pro$^{37}$,Pro$^{38}$[Asp$^{28}$]exendin-4(1-39)-(Lys)$_6$-NH$_2$,
H-Asn-(Glu)$_5$-desPro$^{36}$,Pro$^{37}$,Pro$^{38}$[Asp$^{28}$]exendin-4(1-39)-(Lys)$_6$-NH$_2$,
H-(Lys)$_6$-desPro$^{36}$[Trp(O$_2$)$^{25}$,Asp$^{28}$]exendin-4(1-39)-Lys$_6$-NH$_2$,
H-desAsp$^{28}$ Pro$^{36}$,Pro$^{37}$,Pro$^{38}$[Trp(O$_2$)$^{25}$]exendin-4(1-39)-NH$_2$,
H-(Lys)$_6$-desPro$^{36}$,Pro$^{37}$,Pro$^{38}$[Trp(O$_2$)$^{25}$,Asp$^{28}$]exendin-4(1-39)-NH$_2$,
H-Asn-(Glu)s-desPro$^{36}$,Pro$^{37}$,Pro$^{38}$[Trp(O$_2$)$^{25}$,Asp$^{28}$]exendin-4(1-39)-NH$_2$,
desPro$^{36}$,Pro$^{37}$,Pro$^{38}$[Trp(O$_2$)$^{25}$,Asp$^{28}$]exendin-4(1-39)-(Lys)$_6$-NH$_2$,
H-(Lys)$_6$-desPro$^{36}$,Pro$^{37}$,Pro$^{38}$[Trp(O$_2$)$^{25}$,Asp$^{28}$]exendin-4(1-39)-(Lys)$_6$-NH$_2$,
H-Asn-(Glu)$_5$-desPro$^{36}$,Pro$^{37}$,Pro$^{38}$[Trp(O$_2$)$^{25}$,Asp$^{28}$]exendin-4(1-39)-(Lys)$_6$-NH$_2$,
H-(Lys)$_6$-desPro$^{36}$[Met(O)$^{14}$,Asp$^{28}$]exendin-4(1-39)-Lys$_6$-NH$_2$,
desMet(O)$^{14}$ Asp$^{28}$ Pro$^{36}$, Pro$^{37}$, Pro$^{38}$exendin-4(1-39)-NH$_2$,
H-(Lys)$_6$-desPro$^{36}$,Pro$^{37}$,Pro$^{38}$[Met(O)$^{14}$,Asp$^{28}$]exendin-4(1-39)-NH$_2$,
H-Asn-(Glu)$_5$-desPro$^{36}$,Pro$^{37}$,Pro$^{38}$[Met(O)$^{14}$,Asp$^{28}$]exendin-4(1-39)-NH$_2$,
desPro$^{36}$,Pro$^{37}$,Pro$^{38}$[Met(O)$^{14}$,Asp$^{28}$]exendin-4(1-39)-(Lys)$_6$-NH$_2$,
H-(Lys)$_6$-desPro$^{36}$,Pro$^{37}$,Pro$^{38}$[Met(O)$^{14}$,Asp$^{28}$]exendin-4(1-39)-Lys$_6$-NH$_2$,
H-Asn-(Glu)s-desPro$^{36}$,Pro$^{37}$,Pro$^{38}$[Met(O)$^{14}$,Asp$^{28}$]exendin-4(1-39)-(Lys)$_6$-NH$_2$,
H-(Lys)$_6$-desPro$^{36}$[Met(O)$^{14}$, Trp(O$_2$)$^{25}$,Asp$^{28}$]exendin-4(1-39)-Lys$_6$-NH$_2$,
desAsp$^{28}$Pro$^{36}$,Pro$^{37}$,Pro$^{38}$[Met(O)$^{14}$, Trp(O$_2$)$^{25}$]exendin-4(1-39)-NH$_2$, H-(Lys)$_6$-desPro$^{36}$, Pro$^{37}$, Pro$^{38}$[Met(O)$^{14}$, Trp(O$_2$)$^{25}$, Asp$^{28}$]exendin-4(1-39)-NH$_2$, H-Asn-(Glu)$_5$-desPro$^{36}$,Pro$^{37}$,Pro$^{38}$[Met(O)$^{14}$,Asp$^{28}$]exendin-4(1-39)-NH$_2$, desPro$^{36}$, Pro$^{37}$, Pro$^{38}$[Met(O)$^{14}$, Trp(O$_2$)$^{25}$,Asp$^{28}$]exendin-4(1-39)-(Lys)$_6$-NH$_2$, H-(Lys)$_6$-desPro$^{36}$,Pro$^{37}$,Pro$^{38}$[Met(O)$^{14}$,Trp(O$_2$)$^{25}$, Asp$^{28}$]exendin-4(1-39)-(Lys)$_6$-NH$_2$, H-Asn-(Glu)$_5$-desPro$^{36}$,Pro$^{37}$,Pro$^{38}$[Met(O)$^{14}$,Trp(O$_2$)$^{25}$, Asp$^{28}$]exendin-4(1-39)-(Lys)$_6$-NH$_2$, and pharmaceutically acceptable salts thereof.

In a further aspect a preferred GLP-1 agonist is selected from the group consisting of GLP-1 (in particular GLP-1 (7-36) amide, SEQ ID NO:4), Arg$^{34}$,Lys$^{26}$(N$^\varepsilon$(γ-glutamyl (N$^\alpha$hexadecanoyl)))GLP-1 (7-37) (liraglutide), albiglutide, dulaglutide, semaglutide and pharmaceutically acceptable salts thereof. In particular, a preferred GLP-1 agonist is selected form the group consisting of albiglutide, dulaglutide, semaglutide and pharmaceutically acceptable salts thereof.

A further preferred GLP-1 agonist is lixisenatide (SEQ ID NO:1) as well as its pharmaceutically acceptable salts.

A preferred aspect of the invention relates to a method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature in the range of about 23° C. to about 29° C., wherein the polypeptide is lixisenatide.

Another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature in the range of about 23° C. to about 29° C., wherein the solid phase is a Rink amide resin, and the polypeptide is lixisenatide.

Another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature of about 26° C. to about 29° C.

Another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature in the range of about 26° C. to about 29° C., wherein the polypeptide is lixisenatide.

Another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature in the range of about 26° C. to about 29° C., wherein the solid phase is a Rink amide resin, and the polypeptide is lixisenatide.

Another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature of 26° C.

Another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature of 26° C., wherein the polypeptide is lixisenatide.

Another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature of 26° C., wherein the solid phase is a Rink amide resin, and the polypeptide is lixisenatide.

Yet another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid in an amount of 97% and 1,2-ethanedithiol in an amount of 3%, at a temperature in the range of about 23° C. to about 29° C.

Yet another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid in an amount of 97% and 1,2-ethanedithiol in an amount of 3%, at a temperature in the range of about 23° C. to about 29° C., wherein the polypeptide is lixisenatide.

Yet another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid in an amount of 97% and 1,2-ethanedithiol in an amount of 3%, at a temperature in the range of about 23° C. to about 29° C., wherein the solid phase is a Rink amide resin, and the polypeptide is lixisenatide.

Yet another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid in an amount of 97% and 1,2-ethanedithiol in an amount of 3%, at a temperature in the range of about 26° C. to about 29° C.

Yet another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid in an amount of 97% and 1,2-ethanedithiol in an amount of 3%, at a temperature in the range of about 26° C. to about 29° C., wherein the polypeptide is lixisenatide.

Yet another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid in an amount of 97% and 1,2-ethanedithiol in an amount of 3%, at a temperature in the range of about 26° C. to about 29° C., wherein the solid phase is a Rink amide resin, and the polypeptide is lixisenatide.

Yet another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid in an amount of 97% and 1,2-ethanedithiol in an amount of 3%, at a temperature of 26° C.

Yet another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid in an amount of 97% and 1,2-ethanedithiol in an amount of 3%, at a temperature of 26° C., wherein the polypeptide is lixisenatide.

Yet another preferred aspect of the invention relates to a method for the cleavage of a solid phase-bound polypeptide from the solid phase, the method comprising contacting the solid phase, to which the polypeptide is bound, with a composition consisting essentially of trifluoroacetic acid in an amount of 97% and 1,2-ethanedithiol in an amount of 3%, at a temperature of 26° C., wherein the solid phase is a Rink amide resin, and the polypeptide is lixisenatide.

Yet another aspect of the invention is a method for the solid-phase synthesis of a polypeptide comprising a pre-determined amino acid sequence, said method comprising:
(a) coupling an amino acid building block, comprising an unprotected C-terminal carboxyl group and a protected N-terminal amino group, C-terminally to a solid phase, such as a Rink amide resin,
(b) de-protecting the N-terminal amino group of the amino acid building block,
(c) coupling an amino acid building block, comprising an unprotected C-terminal carboxyl group and a protected N-terminal amino group, C-terminally to the unprotected N-terminal amino of step (b),
(d) optionally repeating steps (b) and (c), and
(e) cleaving the polypeptide from the solid phase by the method of the invention, as described herein.

Amino acid building blocks, suitable in the method of solid phase synthesis of the invention, are described herein.

In the method of solid-phase synthesis of the invention, a second or subsequent cleavage step can be omitted. In the solid phase synthesis of a polypeptide, cleavage step (e) is preferably performed once.

The skilled person knows suitable conditions for coupling in steps (a) or/and (c), and de-protection according to step (b)

The peptide to be synthesized can be a peptide as described herein. In the method of solid phase synthesis, the polypeptide can selected from GLP-1, analogs and derivatives thereof, exendin-3, analogs and derivatives thereof, and exendin-4, analogs and derivatives thereof, as described herein. In particular, the polypeptide is selected from exendin-4 and lixisenatide. A preferred polypeptide is lixisenatide. The polypeptide can also be selected from albiglutide, dulaglutide and semaglutide.

In one aspect the polypeptide to be synthesized is preferably lixisenatide or exendin-4, wherein, after coupling of the amino acid building block Arg(20), Glu (17), Gln(13), Leu(10) or/and Gly(4), a capping step can be performed between steps (c) and (d). According to the present invention, "capping" is the acetylation of a free, unprotected N-terminal amino group to which no amino acid building block has been coupled, in order to terminate chain elongation in these molecules. Such capped molecules can be removed from the product during purification. Capping is described in FIG. 1.

In particular, "capping" according to the present invention means contacting the product obtained in step (c) with a capping reagent or capping composition comprising a capping compound, wherein the capping compound binds to an unprotected N-terminal amino group of the amino acid chain to which no building block has been coupled in step (c).

In one aspect, the capping composition comprises acetic anhydride in a concentration of 0.5-5% v/v. In a preferred aspect the concentration of acetic anhydride is 1-3% v/v, more preferred 2% v/v.

In one aspect, the capping composition comprises diisopropylethylamine, wherein the concentration of diisopropylethylamine can be 0.2-2% v/v and preferably is 0.5-2% v/v. A preferred concentration of diisopropylethylamine is 1% v/v.

In one aspect, the capping composition comprises diisopropylethylamine and acetic anhydride, wherein the concentration of diisopropylethylamine can be 0.2-2% v/v and preferably is 0.5-2% v/v, and the concentration of acetic anhydride can be 0.5-5% v/v and preferably is 1-3% v/v.

It is preferred that the capping composition comprises 2% v/v acetic anhydride and 1% v/v diisopropylethylamine.

Capping can be performed for 5 to 15 min, in particular about 10 min.

Preferred capping is performed for about 10 min with a capping reagent or capping composition comprising 2% v/v acetic anhydride and 1% v/v diisopropylethylamine.

The capping reaction according to the invention can be performed at room temperature. Room temperature according to the invention is related to a temperature between approximately 15-25° C., a temperature ranging from approximately 20-23° C., a temperature ranging from approximately 19-21° C. or a temperature of approximately 20° C.

The solvent used in the capping step is preferably a polar non-aqueous solvent, such as acetonitrile, dimethyl sulfoxide (DMSO), methanol, methylene chloride, N,N-dimethylacetamide (DMA), N,N-dimethylformamide (DMF), N-methylpyrrolidone, or mixtures thereof. In a preferred aspect, the solvent used in the capping step is DMF.

Yet another aspect of the invention is a composition, consisting essentially of trifluoroacetic acid and 1,2-ethanedithiol, wherein the composition comprises trifluoroacetic acid in an amount of 95 to 99% v/v, and 1,2-ethanedithiol in an amount of 1 to 5% v/v.

More particular, the composition of the invention essentially consists of trifluoroacetic acid in an amount of about 97% v/v, and 1,2-ethanedithiol in an amount of about 3% v/v.

Another preferred composition essentially consists of trifluoroacetic acid and 1,2-ethanedithiol in ratio of 8.25: 0.25 (v:v).

Further features of the composition are described above in connection with the method of the invention. In particular, the composition of the invention can be used in a solid-phase synthesis of a polypeptide, as described herein, to cleave the polypeptide from the solid phase, as described herein.

Abbreviations

Ac(N1-N2): N-terminally acetylated fragment of a polypeptide from position N1 to N2.

H(N1-N2) or (N1-N2): Fragment of a polypeptide from position N1 to N2 comprising a free, N-terminal amino function.

Fmoc(N1-N2): Fragment of a polypeptide from position N1 to N2 comprising a protected N-terminal amino function, wherein the protective group is Fmoc.

(N−1)-impurity: Relates to the occurrence of an unintended peptide during peptide synthesis, which lacks a building block at a certain position. In case the intended synthesized polypeptide has a length N, the impurity has a length of N−1. The occurrence of (N−1) impurities is prevented by capping.

Fmoc fluorenylmethoxycarbonyl
Boc tert-butoxycarbonyl
Bzl benzyl
Pbf 2,2,5,7,8-pentamethyldihydrobenzofuran-5-sulfonyl
tBu tert-butyl
OtBu O-tert-butyl
Trt trityl
DIPE diisopropylether The invention is further characterized by the following Figures and Examples.

FIGURES

FIG. 1: Solid phase synthesis of peptides.

FIG. 2: Sequence of lixisenatide (SEQ ID NO:1), exendin-4 (SEQ ID NO:2), exendin-3 (SEQ ID NO:3) and GLP-1 (GLP-1(7-36) amide, SEQ ID NO:4).

FIG. 3: Occurrence of acetylated erroneous sequences during synthesis of lixisenatide. Coupling of Fmoc-Arg(20)-OH and subsequent capping/Fmoc cleavage. It should be noted that the position 21 (Leu) was omitted from the synthesis. (1) Fmoc-(22-44)+Arg, (2) (22-44)+Arg, (3) Ac(22-44)+Arg, (4) Fmoc-(22-44)+Arg+Val. The data show that the acetylated fragments have already been formed during the capping step, however, the wrong position is acetylated [Ac(22-24)+Arg is already occurring during capping of Arg].

FIG. 4: Occurrence of acetylated erroneous sequences during synthesis of lixisenatide. Coupling of Fmoc-Gln(13)-OH and subsequent capping/Fmoc cleavage. (1) Ac(14-44), (2) Fmoc(13-44), (3) Ac(13-44), (4) (13-44), (5) (14-44). The data show that the acetylated fragments have already been formed during the capping step, however, the wrong position is acetylated (Ac(13-44)).

FIG. 5: Occurrence of acetylated erroneous sequences during synthesis of lixisenatide. Coupling of Fmoc-Lys(12)-OH and subsequent capping/Fmoc cleavage. (1) Ac(13-44), (2) Fmoc(12-44), (3) Ac(12-44), (4) (12-44). The data show that the acetylated fragments have already been formed during the capping step, however, the wrong position is acetylated (Ac(12-44)).

FIGS. 6A-6C: Comparison of the synthesis of lixisenatide using the method of capping according to the invention (FIG. 6B) in comparison to capping with 10% acetic anhydride and 5% v/v DIPEA in DMF for 20 min (FIG. 6A) by means of HPLC chromatography. (FIG. 6C) overlap of HPLC chromatograms of (FIG. 6A) and (FIG. 6B).

FIG. 7: HPLC of lixisenatide (raw product). Red: undesired acetylated by-products.

FIG. 8: Ac(36-44) formation, depending upon the capping cocktail and temperature.

FIG. 9: Ac(23-44) formation, depending upon the capping cocktail and temperature.

FIG. 10: Ac(21-44) formation, depending upon the capping cocktail and temperature.

FIG. 11: Ac(19-44) formation, depending upon the capping cocktail and temperature.

FIG. 12: Ac(18-44) formation, depending upon the capping cocktail and temperature.

FIG. 13: Ac(15-44) formation, depending upon the capping cocktail and temperature.

FIG. 14: Ac(12-44) formation, depending upon the capping cocktail and temperature.

FIG. 15: Ac(8-44) formation, depending upon the capping cocktail and temperature.

FIG. 16: Ac(6-44) formation, depending upon the capping cocktail and temperature.

FIG. 17: Comparison of Ac(X-44) content in capping at 9 different positions in the lixisenatide synthesis at 15° C., room temperature (RT) and 30° C.

FIG. 18: Comparison of Ac[(X-1)-44] content in capping at 9 different positions in the lixisenatide synthesis at 15° C., room temperature (RT) and 30° C.

FIG. 19: Comparison of Ac(X-44) content in capping under different conditions, or without capping, at 9 different positions in the lixisenatide synthesis under different capping conditions.

FIG. 20: Comparison of Ac[(X-1)-44] content in capping under different conditions, or without capping, at 9 different positions in the lixisenatide synthesis under different capping conditions.

EXAMPLE 1

Synthesis of Lixisenatide

The active substance Lixisenatide is a polypeptide amide composed of 44 amino acids; acetate functions as counterion.

In the one-letter code, the amino acid sequence of Lixisenatide is as follows:

H-G-E-G-T-F-T-S-D-L-S-K-Q-M-E-E-E-A-V-R-L-F-I-E-W-
L-K-N-G-G-P-S-S-G-A-P-P-S-K-K-K-K-K-K-NH$_2$

The peptide chain was constructed by means of linear solid-phase synthesis, starting from the C-terminus, Lys-44.

The method of synthesis is Fmoc solid-phase peptide synthesis, in which a Rink amide resin was used in order to obtain a peptide amide. The reactions were carried out in DMF at room temperature. Between the reactions, washing was carried out repeatedly, mostly with DMF, with one of the middle washing steps being carried out with isopropanol.

The synthesis of Lixisenatide on the polymeric support can be broken down into the following steps:
Coupling of the first Fmoc-amino acid (Fmoc-Lys(Boc)-OH) to Rink resin
Capping of the unreacted amino group
Cleavage of the temporary protecting group Fmoc
Coupling of the further Fmoc-amino acids or Fmoc-dipeptides
Capping of the unreacted amino group
Final Fmoc cleavage
Cleavage of Lixisenatide from the resin and simultaneous removal of the side chain protecting groups The synthesis cycle is illustrated in FIG. 1.

1.1 Coupling of the First Fmoc-Amino Acid (Fmoc-Lys (Boc)-OH) to Rink Resin

Before the synthesis began, the Rink amide resin was swollen in DMF. The swelling was carried out for 2-15 h. Subsequently, the temporary protecting group Fmoc was cleaved from the Rink amide resin using 25% piperidine in DMF. This cleavage was undertaken twice; cleavage time of 5 minutes and 20 minutes. Following the Fmoc cleavage, the resin was washed repeatedly with DMF and once with isopropanol.

The coupling of the first Fmoc-amino acid, Fmoc-Lys (Boc)-OH, was carried out in an excess of 2.4 eq, in order to load the resin. HOBt hydrate, HBTU and DIPEA served as coupling reagents. The coupling time was 60-120 min.

In order to completely load the Rink resin with Fmoc-Lys(Boc)-OH, a further loading was carried out with the coupling reagents HOBt hydrate and DIC. The coupling time was 6-18 h. The mixture was stirred while step 1.1 was carried out. The capping was subsequently carried out.

1.2 Capping of the Unreacted Amino Group

The consequence of incomplete loading of the resin is that as yet unreacted amino groups are found on the resin. These were inactivated, and hence made unavailable for further coupling, by adding a mixture of acetic anhydride/DIPEA/DMF (10:5:85). The capping mixture remained on the resin for 20 minutes while stirring. The remaining free amino group is acylated. Subsequently, the resin was washed repeatedly with DMF and once with isopropanol.

A capping method according to the invention at least at 5 positions of a Lixisenatide synthesis is described in examples 4 and 5.

1.3. Cleavage of the Temporary Protecting Group Fmoc

The temporary protecting group Fmoc was cleaved using 25% piperidine in DMF. This cleavage was undertaken twice; cleavage time of 5 minutes and 20 minutes. Following the Fmoc cleavage, the resin was washed repeatedly with DMF and once with isopropanol.

1.4 Coupling of the Further Fmoc-Amino Acids or Fmoc-Dipeptides

The next Fmoc-amino acid was coupled to the deprotected amino group on the resin. The coupling was carried out in DMF at different equivalents. The coupling times were between 2 h and 18 h. HOBt/DIC, and also HBTU/DIPEA, were used as coupling reagents.

The following derivatives were used as Fmoc-amino acids:

Fmoc-Lys(Boc)-OH
Fmoc-Ser(tBu)-OH
Fmoc-Pro-OH
Fmoc-Ala-OH×$H_2O$
Fmoc-Gly-OH
Fmoc-Asn(Trt)-OH
Fmoc-Leu-OH
Fmoc-Trp(Boc)-OH
Fmoc-Glu(OtBu)-OH×$H_2O$
Fmoc-Ile-OH
Fmoc-Phe-OH
Fmoc-Arg(Pbf)-OH
Fmoc-Val-OH
Fmoc-Met-OH
Fmoc-Gln(Trt)-OH
Fmoc-Asp(OtBu)-OH
Fmoc-Thr(tBu)-OH
Fmoc-His(Trt)-OH Alternatively, it was also possible to use Fmoc-dipeptides (method according to the invention):

Fmoc-Pro-Pro-OH (CAS 129223-22-9)
Fmoc-Ala-Pro-OH (CAS 186023-44-9)
Fmoc-Ser(tBu)-Gly-OH (CAS 113247-80-6)
Fmoc-Gly-Pro-OH (CAS 212651-48-4)
Fmoc-Gly-Gly-OH (CAS 35665-38-4)
Fmoc-Asn(Trt)-Gly-OH (from Bachem B-3630)
Fmoc-Glu(OtBu)-Gly-OH (CAS 866044-63-5)
Fmoc-His(Trt)-Gly-OH If the coupling was found to be incomplete according to the Kaiser test (E. Kaiser et al, Anal. Biochem. 34, 1970, 595), further coupling was possible. For this purpose, the Fmoc-amino acid was coupled again, together with HBTU/DIPEA/HOBt hydrate.

1.5 Capping of the Unreacted Amino Group

See description under point 1.2.

1.6 Final Fmoc Cleavage

The final Fmoc cleavage was carried out as described under point 1.3. The resin was finally washed again with diisopropyl ether and dried under reduced pressure.

1.7 Cleavage of Lixisenatide from the Resin and Simultaneous Removal of the Side Chain Protecting Groups The cleavage of Lixisenatide from the Rink resin was carried out as described in example 6.

1.8 Synthesis of Lixisenatide with Inventive Use of Dipeptides

The coupling of the first Fmoc-Lys(Boc)-OH to the resin was carried out with HBTU/DIPEA/HOBt hydrate. After the coupling of the first amino acid Fmoc-Lys(Boc)-OH to the free amine of the Rink amide resin, the following process steps were conducted in an endlessly repeating cycle (see also steps 1.3 to 1.6):

Fmoc cleavage
Coupling
Further coupling, if necessary
Capping
After coupling of the final amino acid unit, the N-terminal Fmoc group is cleaved.

Standard Fmoc-protected amino acids were coupled with DIC/HOBt, with the excess of amino acids and coupling reagents being between 2 and 4 equivalents.

At the positions Pro(36) and Pro(37), instead of two Fmoc-Pro-OH amino acid derivatives, the dipeptide Fmoc-Pro-Pro-OH was coupled with HBTU/DIPEA.

At the position Pro(31), coupling was carried out with HBTU/DIPEA/HOBt hydrate.

At the positions His(1) and Gly(2), instead of the amino acid derivatives Fmoc-His(Boc)-OH and Fmoc-Gly-OH, the dipeptide Fmoc-His(Trt)-Gly-OH was coupled.

After the couplings, the capping was carried out in each case with $Ac_2O$/DIPEA, as is described in examples 4 and 5.

The Fmoc cleavage was performed with 25% piperidine in DMF, in each case successively first with 5 minutes of reaction time, then with 20-40 minutes of reaction time.

The completeness of the coupling was checked by means of a Kaiser test.

After the last coupling and last cleavage of the Fmoc group, the resin was washed, firstly repeatedly with DMF, then with isopropanol and finally with diisopropyl ether, and it was subsequently dried at 35° C. under reduced pressure.

The cleavage of the raw peptide from the resin was carried out in trifluoroacetic acid with scavengers such as 1,2-ethanedithiol.

The raw peptide was purified in a two-step HPLC process with C18 RP silica gel as solid phase. In the first purification step, a buffer system with acetonitrile/water with 0.1% TFA was used; in the second step, a buffer system with acetonitrile/water with AcOH was used. After concentration of the pooled solutions, the pure peptide was obtained by freeze-drying.

Use of 3500 g of Rink amide resin with a loading of 0.3 mmol/g (i.e. a 1.05 mol batch) gave 9970 g of peptide on resin. 4636 g of raw peptide were obtained therefrom.

After purification, 576 g of pure peptide were obtained therefrom. MS: 4855.5 (monoisotopic molar mass); found 4855.6. Amino acid sequencing: correct sequence found. Assay: 89.0% (as is).

1.9 Synthesis of Lixisenatide without Use of Dipeptides

The peptide chain was constructed by means of linear solid-phase synthesis, starting from the C-terminus, Lys-44.

Standard Fmoc-protected amino acids were coupled with DIC/HOBt, with the excess of amino acids and coupling reagents being between 2 and 4 equivalents.

At the positions Pro(37), Pro(36), Pro(31), coupling was carried out with HBTU/DIPEA/HOBt hydrate.

Each coupling was followed by capping with $Ac_2O$/DIPEA. The Fmoc cleavage was performed with 25% piperidine in DMF, in each case successively first with 5 minutes of reaction time, then with 20 minutes of reaction time.

The completeness of the coupling was checked by means of a Kaiser test. After the last coupling and last cleavage of the Fmoc group, the resin was washed, firstly repeatedly with DMF, then with isopropanol and finally with diisopropyl ether, and it was subsequently dried at 35° C. under reduced pressure.

The cleavage of the raw peptide from the resin was carried out in trifluoroacetic acid with scavengers such as 1,2-ethanedithiol, thioanisole, phenol and water.

The raw peptide was purified in a two-step HPLC process with C18 RP silica gel as solid phase. After concentration of the pooled solutions, the pure peptide was obtained by freeze-drying. Table 1 compares the contents of racemized D-His-Lixisenatide and the contents of some impurities in the pure peptide between the synthesis using the dipeptides and without the dipeptides.

TABLE 1

Comparison of the Lixisenatide syntheses with and without use of the dipeptides.

| | Content of D-His | Content of desGly(2)-Lixisenatide | Content of desPro(36)-Lixisenatide | Content of diPro(36)-Lixisenatide |
|---|---|---|---|---|
| Synthesis of lixisenatide with dipeptides Fmoc-His(Trt)-Gly-OH, Fmoc-Pro-Pro-OH according to the invention | 0.41% | Not present | Not present | Not present |
| Comparative synthesis of lixisenatide without dipeptides | 4.1% | 2.5% | 1% | 1% |

The data show that the use of the dipeptide Fmoc-His(Trt)-Gly-OH gives a Lixisenatide which does not contain elevated values of D-His arising from racemization. Moreover, when using Fmoc-His(Trt)-Gly-OH, desGly(2)-Lixisenatide is no longer found. Furthermore, the N−1 and N+1 peptides in the vicinity of the chain position Pro(36) and Pro(37) (e.g. desPro(36)-Lixisenatide or diPro(36)Lixisenatide) did not occur.

EXAMPLE 2

Synthesis, Purification and Characterization of Exendin-4 (According to the Invention)

The active substance Exendin-4 is a polypeptide amide composed of 39 amino acids; acetate functions as counterion.

In the one-letter code, the amino acid sequence is as follows:

H-G-E-G-T-F-T-S-D-L-S-K-Q-M-E-E-E-A-V-R-L-F-I-E-W-L-K-N-G-G-P-S-S-G-A-P-P-P-S-$NH_2$

MW 4186.66 g/mol; MW (monoisotopic)=4184.03 g/mol.

The synthesis of Exendin-4 was carried out precisely as described in the synthesis of Lixisenatide, according to the abovementioned sequence. At positions 1 and 2, coupling was carried out in one cycle with Fmoc-His(Trt)-Gly-OH. At positions 37 and 38, coupling was carried out in one cycle with Fmoc-Pro-Pro-OH. At the other positions, coupling was carried out with Fmoc-amino acids (monoamino acid units).

Use of 26.666 g of Rink amide resin with a loading of 0.42 mmol/g (i.e. a 11.2 mmol batch) gave 74 g of peptide on resin. From this, 65 g of peptide on resin were cleaved, and 28 g of raw peptide were obtained. For the purification, from this, 21.3 g of raw peptide were used, and 4.01 g of pure peptide were obtained. MS: 4184.03 (monoisotopic molar mass): found 4185.1 [M+H]. Purity 98.25 Fl %.

The use of the dipeptides confirms the results which were obtained for Lixisenatide. The use of the dipeptide Fmoc-His(Trt)-Gly-OH gives an Exendin-4 which does not contain elevated values of D-His arising from racemization. Moreover, when using Fmoc-His(Trt)-Gly-OH, desGly(2)-Exendin-4 is no longer found. Furthermore, the N−1 and N+1 peptides in the vicinity of the chain position Pro(36) and Pro(37) (e.g. desPro(36)-Exendin-4 or diPro(36)Exendin-4) did not occur.

EXAMPLE 3

Synthesis of Fmoc-His(Trt)-Gly-OH 3.1 Fmoc-His(Trt)-Gly-OBzl

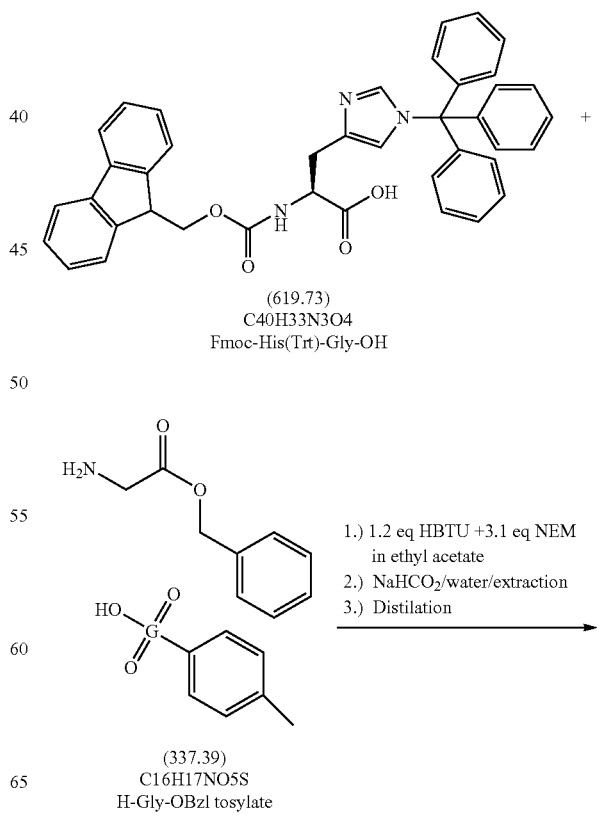

(619.73)
C40H33N3O4
Fmoc-His(Trt)-Gly-OH

1.) 1.2 eq HBTU +3.1 eq NEM in ethyl acetate
2.) $NaHCO_2$/water/extraction
3.) Distillation (337.39)
C16H17NO5S
H-Gly-OBzl tosylate

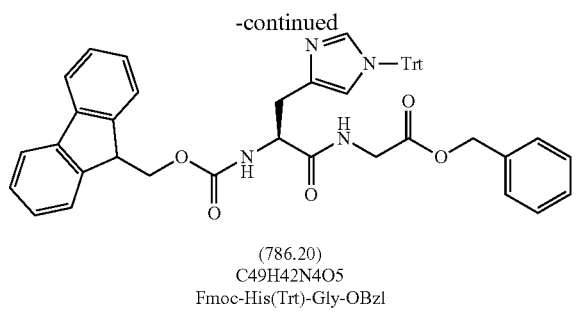

(786.20)
C49H42N4O5
Fmoc-His(Trt)-Gly-OBzl 40 g of Fmoc-His(Trt)-OH were dissolved together with 32.7 g of H-Gly-OBzl tosylate and 29.37 g of HBTU in 400 ml of ethyl acetate. Thereafter, 33.32 ml of N-ethylmorpholine were added. The reaction was stirred for 4 h at 30° C. Thereafter, extraction was carried out three times with 256 g of an 8% sodium bicarbonate solution each time, and then washing was carried out once with 250 ml of water. Half of the resulting ethyl acetate solution was evaporated and processed further in the next step.

3.2 Fmoc-His(Trt)-Gly-OH

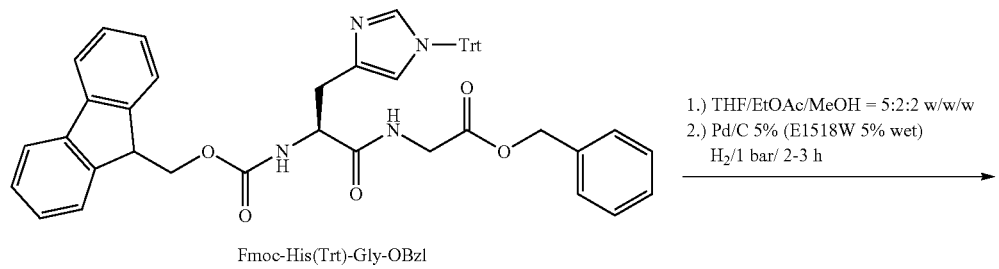

Fmoc-His(Trt)-Gly-OBzl

1.) THF/EtOAc/MeOH = 5:2:2 w/w/w
2.) Pd/C 5% (E1518W 5% wet)
   $H_2$/1 bar/ 2-3 h

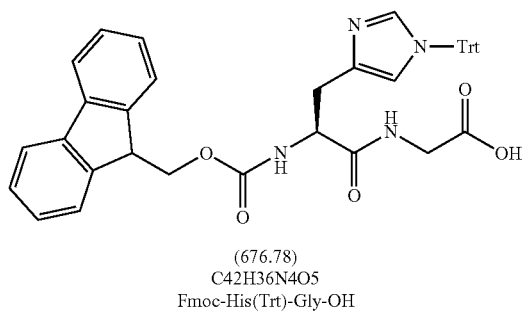

(676.78)
C42H36N4O5
Fmoc-His(Trt)-Gly-OH

THF and methanol were added to the ethyl acetate phase, such that a 5:2:2 (w/w/w) THF/ethyl acetate/MeOH mixture was formed. Subsequently, 10 g of palladium on carbon catalyst (5%) were added, and this mixture was hydrogenated at 30° C. and a hydrogen pressure of 1.1 bar for 2.5 h. Thereafter, the catalyst was filtered off and the resulting solution was evaporated until a precipitate began to form. Subsequent stirring was carried out for 1 h and the solution was left to stand at room temperature for 4 days. The product was filtered off and subsequently extracted by stirring in 2-butanone at 80° C. for 4 h. Yield: 32.9 g of Fmoc-His(Trt)-Gly-OH (75%).

EXAMPLE 4

Acetylated Erroneous Sequences During the Synthesis of Lixisenatide 4.1 Determining the Content of Acetylated Erroneous Sequences During the Synthesis of Lixisenatide Some acetylated erroneous sequences can be seen in the HPLC profile of the crude Lixisenatide product. These usually arise from unreacted amino groups on the resin being capped. What is achieved by the capping is that no (N−1) impurities can occur, which differ only slightly from the desired product and are hence difficult to remove by purification.

The completeness and also the coupling kinetics at selected positions were monitored by Edman degradation. A resin sample was taken from the synthesis of Lixisenatide and the Fmoc group was cleaved therefrom. This resin sample was then subjected to Edman degradation and in this way it was possible to determine the ratio of coupled amino acid to the (N−1) amino acid, from which the coupling yield could be directly inferred. The results of the Edman degradation (table 2) show high coupling values. These values are so high that they cannot account for the amounts of acetylated erroneous sequences (HPLC data in table 2). This means that there must be an alternative way of forming these by-products. The elucidation of this situation will be described in the following sections.

TABLE 2

Coupling yields and contents of acetylated fragments during synthesis of Lixisenatide. The percentage contents of acetylated erroneous sequences from HPLC data and Edman results (coelution of Ac(6-44), Ac(5-44) and Ac(4-44)) are compared to one another.

| Impurity | Amino acid to be coupled | Coupling yield (Edman data) | Impurities content (HPLC) |
| --- | --- | --- | --- |
| Ac(36-44) | Ala(35) | 99.4-99.5% | 4.7% |
| Ac(23-44) | Phe(22) | >98.4% | 0.9% |
| Ac(20-44) | Val(19) | 99.7% | 2.0% |
| Ac(13-44) | Lys(12) | 98.7-99.5% | 2.1% |
| Ac(6-44) | Thr(5) | 98.4-99.5% | Approx. 4.3% |
| Ac(5-44) | Gly(4) | 99.1-99.8% | |
| Ac(4-44) | Glu(3) | 98.2-99.4% | |

4.2 Formation of Acetylated Erroneous Sequences

In order to investigate the points in the synthesis cycle at which the acetylated erroneous sequences are formed, resin samples were taken over a coupling cycle, and the peptide was cleaved and investigated using LC-MS. These investigations were carried out at the positions of coupling of Fmoc-Arg(20)-OH and coupling of Fmoc-Gln(13)-OH.

In the coupling of Fmoc-Arg(20)-OH to the solid-phase-bonded peptide of the Lixisenatide partial sequence H(22-24), samples were taken after coupling times of 1 h, 2 h, 4 h, 8 h and 24 h and also after capping, the subsequent Fmoc cleavage and the coupling of valine(19). As can be seen in FIG. 3, the erroneous sequence Ac(22-44)+Arg occurred for the first time during the capping step (3.1%). During the capping, therefore, a small portion of the Fmoc group was cleaved (lost) and immediately acylated. In order to explain the designation Ac(22-24)+Arg, it should be noted that the position 21 (Leu) was omitted from the synthesis.

The same experiment was conducted for the coupling of Fmoc-Gln(13)-OH during the Lixisenatide synthesis (FIG. 4). In this case, the erroneous sequence Ac(13-44) was observed (4.6%) for the first time during the Fmoc cleavage after the coupling and the capping of glutamine(13). In the remaining course of the synthesis after the coupling of Fmoc-Lys(12)-OH, it can be seen that Ac(12-44) was also formed (4.1%) during the capping (see FIG. 5).

The experiment shows that it is necessary to search for capping conditions, under which the undesired formation of the acetylated erroneous sequence of the Nth amino acid (the last one coupled) is prevented, without the capping ability of the mixture used being reduced to such a significant extent that a potential (N−1) impurity is no longer capped.

4.3 Variation in the Capping Conditions

The couplings of Fmoc-Arg(20)-OH, Fmoc-Leu(10)-OH, Fmoc-Gly(4)-OH and Fmoc-Thr(5)-OH were investigated. Various capping conditions were compared to one another.

The capping conditions were varied in a laboratory synthesis of Lixisenatide. Particular attention was paid to the contents of undesired Ac(N-44) and desired Ac([N−1]-44). The conditions tested are as follows:

10% acetic anhydride/5% DIPEA in DMF for 20 minutes
10% acetic anhydride/5% DIPEA in DMF for 10 minutes
2% acetic anhydride/1% DIPEA in DMF for 20 minutes
2% acetic anhydride/1% DIPEA in DMF for 10 minutes The investigations were carried out at the positions Arg (20), Leu(10), Thr(5) and Gly(4). The results are compiled in tables 3-6.

The data were also compared with the result of a GMP synthesis of Lixisenatide ("GMP capping" in tables 3-6). The capping conditions corresponded to the conditions 10% acetic anhydride/5% DIPEA in DMF. The contact time of the resin with the capping mixture in the GMP batch was 7-8 minutes longer, and was therefore 27-28 minutes. This arose from the longer time taken to pump the capping mixture away.

4.3.1 Coupling at Position Arg(20)

Fmoc-Arg(Pbf)-OH was coupled to Leu(21). On those chains on which no coupling took place (product H(21-44)), the product Ac(21-44) was formed by the subsequent capping. Both products Ac(20-44) and H(20-44) are formed when, during capping, the Fmoc group is undesirably cleaved (formation of H(20-44)) and acetylation occurs (formation of Ac(2044)).

It can be clearly seen in table 3 that the degree of formation of the undesired products H(20-44) and Ac(20-44) is dependent both on the capping time and on the amount of acetic anhydride and DIPEA (see Ac(20-44)% column). The highest percentage value can be seen in the GMP capping. The lowest content of Ac(20-44) is found under the conditions "2% acetic anhydride/1% DIPEA in DMF for 10 minutes".

The capping power of the various capping mixtures (and hence the original intended use) is approximately the same (see column Ac(21-44)), i.e. all capping mixtures convert H(21-44)). The mixture "2% acetic anhydride/1% DIPEA in DMF for 10 minutes" also fulfils the desired purpose of avoiding (N−1) impurities.

TABLE 3

Results of the coupling of Fmoc-Arg(Pbf)-OH at position 20. The table shows the content of acetylated and non-acetylated fragments depending on the capping conditions. The results were obtained by means of LC-MS. The data were compared with the results from a GMP synthesis ("GMP capping").

| Capping conditions | Ac(20-44)% | Fmoc(20-44)% | H(20-44)% | H(21-44)% | Ac(21-44)% |
| --- | --- | --- | --- | --- | --- |
| 10 min/2% acetic anhydride, 1% DIPEA | 0.75 | 96.48 | 0.08 | 0.66 | 2.03 |
| 10 min/10% acetic anhydride, 5% DIPEA | 0.92 | 95.87 | 0.55 | 0.69 | 1.96 |
| 20 min/2% acetic anhydride, 1% DIPEA | 1.63 | 95.83 | 0.14 | 0.55 | 1.85 |
| 20 min/10% acetic anhydride, 5% DIPEA | 2.26 | 95.32 | 0.06 | 0.60 | 1.77 |
| GMP capping | 2.64 | 94.47 | 0.03 | 0.68 | 2.18 |

4.3.2 Coupling at the Positions Leu(10), Gly(4) and Thr(5)

The results for Leu(10) are given in table 4 and confirm the results which were obtained for position Arg(20). The content of undesired products Ac(10-44) and H(10-44), which are formed during the capping of the free amino groups of the product H(11-44), is lowest under the conditions "2% acetic anhydride, 1% DIPEA for 10 minutes". The capping power is comparable in the different capping mixtures.

TABLE 4

Results of the coupling of Fmoc-Leu-OH at position 10. The table shows the content of acetylated and non-acetylated fragments depending on the capping conditions. The results were obtained by means of LC-MS.

| Capping conditions | Ac(10-44)% | Fmoc(10-44)% | H(10-44)% | H(11-44)% | Ac(11-44)% |
|---|---|---|---|---|---|
| 10 min/2% acetic anhydride, 1% DIPEA | 0.06 | 98.90 | 0.42 | 0.18 | 0.43 |
| 10 min/10% acetic anhydride, 5% DIPEA | 0.20 | 98.57 | 0.61 | 0.16 | 0.46 |
| 20 min/2% acetic anhydride, 1% DIPEA | 0.13 | 98.24 | 0.90 | 0.18 | 0.56 |
| 20 min/10% acetic anhydride, 5% DIPEA | 0.45 | 98.44 | 0.52 | 0.15 | 0.44 |

For the coupling of Gly(4) as well, the contents of the undesired products Ac(4-44) are dependent on the capping mixture and the reaction time. The capping power is the same in the different mixtures (table 5).

TABLE 5

Results of the coupling of Fmoc-Gly-OH at position 4. The table shows the content of acetylated and non-acetylated fragments depending on the capping conditions. The results were obtained by means of LC-MS.

| Capping conditions | Ac(4-44)% | Fmoc(4-44)% | H(4-44)% | H(6-44)% | Ac(5-44)% |
|---|---|---|---|---|---|
| 10 min/2% acetic anhydride, 1% DIPEA | 0.09 | 98.21 | 0.55 | 0.56 | 0.61 |
| 10 min/10% acetic anhydride, 5% DIPEA | 0.26 | 98.42 | 0.39 | 0.41 | 0.52 |
| 20 min/2% acetic anhydride, 1% DIPEA | 0.10 | 98.40 | 0.47 | 0.36 | 0.67 |
| 20 min/10% acetic anhydride, 5% DIPEA | 0.39 | 98.02 | 0.43 | 0.39 | 0.77 |
| GMP capping | 0.92 | 97.54 | 0.51 | 0.40 | 0.63 |

In addition to the positions Arg(20), Leu(10) and Gly(4), the position Thr(5) was also investigated. In contrast to the three former positions, the contents of the undesired product Ac(N-44) (Ac(5-44) at position 5) are approximately the same under the various capping conditions. However, the capping power of the different mixtures is also comparable here (table 6).

TABLE 6

Results of the coupling of Fmoc-Thr(tBu)-OH at position 5. The table shows the content of acetylated and non-acetylated fragments depending on the capping conditions. The results were obtained by means of LC-MS.

| Capping conditions | Ac(5-44)% | Fmoc(5-44)% | H(5-44)% | H(6-44)% | Ac(6-44)% |
|---|---|---|---|---|---|
| 10 min/2% acetic anhydride, 1% DIPEA | 0.04 | 97.80 | 0.33 | 0.24 | 1.58 |
| 10 min/10% acetic anhydride, 5% DIPEA | 0.07 | 97.93 | 0.15 | 0.24 | 1.61 |
| 20 min/2% acetic anhydride, 1% DIPEA | 0.03 | 97.69 | 0.36 | 0.23 | 1.70 |
| 20 min/10% acetic anhydride, 5% DIPEA | 0.03 | 97.70 | 0.42 | 0.29 | 1.55 |
| GMP capping | 0.07 | 97.77 | 0.25 | 0.24 | 1.67 |

4.3.3 Summary

At the positions Arg(20), Leu(10) and Gly(4), the mild capping mixture (2% acetic anhydride/1% DIPEA in DMF for 10 minutes) is sufficient in order to maintain the desired effect of avoiding (N−1) impurities by acylation. However, in these three cases, the respective formation of Ac(20-44), Ac(10-44) and Ac(4-44) is dependent on the capping time and also on the capping mixture. This does not apply to the position Thr(5).

EXAMPLE 5

Synthesis of Lixisenatide

The example relates to the synthesis of Lixisenatide (cf. SEQ ID NO:1). At the start of the synthesis, the solid-phase-bonded linker bears an Fmoc protecting group. The individual amino acid units were coupled starting from the C-terminus (position 44) towards the N-terminus in coupling cycles, which consist of the steps of Fmoc cleavage Coupling of the Fmoc-protected amino acid unit and Capping.

At the positions Arg(20), Glu(17), Gln(13), Leu(10) and Gly(4), the capping method according to the invention (2% acetic anhydride/1% DIPEA in DMF for 10 minutes) was used. For these positions, the instructions for a coupling cycle are described below. At the other positions, capping was carried out with 10% acetic anhydride/5% DIPEA in DMF for 20 minutes. This capping is described, by way of example, at the position Thr(5). The capping method according to the invention comprises milder conditions.

The batch size was 1050 mmol of Rink resin.

5.1. Coupling of Fmoc-Arg(Pbf)-OH at Position 20

5.1.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 30 minutes; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.1.2 Coupling of Fmoc-Arg(Pbf)-OH 21 l of DMF were added to the reactor. Thereafter, 2.125 kg of FmocArg(Pbf)-OH were weighed in and 5.3 l of DMF were added. After complete dissolution, this solution was emptied into the reactor, followed by a solution of 502 g hydroxybenzotriazole hydrate (HOBt hydrate) in 2.2 l of DMF. Finally, 413 g of N,N-diisopropylcarbodiimide (DIC) were added to the reactor. The coupling time was 6-18 h. After coupling, the solvent was filtered off from the resin by suction and the capping was immediately continued.

5.1.3 Capping (According to the Invention)

The reactor was filled with 26.3 l of DMF. At the same time, 1.2 l of DMF, 0.53 l of acetic anhydride and 0.26 l of diisopropylethylamine (DIPEA) were mixed in a 2 l Schott bottle and added to the resin in the reactor. The reactor was stirred for 10 minutes, then filtering with suction was carried out. After the capping, the resin was washed 5 times in the following sequence: DMF (24 l), isopropanol (31.1 l), DMF (8 l), DMF (31.5 l), DMF (31.5 l). The reactor here was filled each time with the respective washing solvent, then stirring was carried out for 3 minutes and filtering with suction was carried out again.

5.2. Coupling of Fmoc-Glu(OtBu)-OH Hydrate at Position 17

5.2.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 30 min; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.2.2 Coupling of Fmoc-Glu(OtBu)-OH Hydrate 21 l of DMF were added to the reactor. Thereafter, 1.453 kg of FmocGlu(OtBu)-OH hydrate were weighed in and 5.3 l of DMF were added. After complete dissolution, this solution was emptied into the reactor, followed by a solution of 502 g hydroxybenzotriazole hydrate (HOBt hydrate) in 2.2 l of DMF. Finally, 413 g of N,N-diisopropylcarbodiimide (DIC) were added to the reactor. The coupling time was 6-18 h. After coupling, the solvent was filtered off from the resin by suction and the capping was immediately continued.

5.2.3 Capping (According to the Invention)

The reactor was filled with 26.3 l of DMF. At the same time, 1.2 l of DMF, 0.53 l of acetic anhydride and 0.26 l of diisopropylethylamine (DIPEA) were mixed in a 2 l Schott bottle and added to the resin in the reactor. The reactor was stirred for 10 minutes, then filtering with suction was carried out. After the capping, the resin was washed 5 times in the following sequence: DMF (24 l), isopropanol (31.1 l), DMF (8 l), DMF (31.5 l), DMF (31.5 l). The reactor here was filled each time with the respective washing solvent, then stirring was carried out for 3 minutes and filtering with suction was carried out again.

5.3 Coupling of Fmoc-Gln(Trt)-OH at Position 13

5.3.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 35 minutes; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.3.2 Coupling of Fmoc-Gln(Trt)-OH 21 l of DMF were added to the reactor. Thereafter, 2.001 kg of FmocGln(Trt)-OH were weighed in and 5.3 l of DMF were added. After complete dissolution, this solution was emptied into the reactor, followed by a solution of 502 g of hydroxybenzotriazole hydrate (HOBt hydrate) in 2.2 l of DMF. Finally, 413 g of N,N-diisopropylcarbodiimide (DIC) were added to the reactor. The coupling time was 6-18 h. After coupling, the solvent was filtered off from the resin by suction and the capping was immediately continued.

5.3.3 Capping (According to the Invention)

The reactor was filled with 26.3 l of DMF. At the same time, 1.2 l of DMF, 0.53 l of acetic anhydride and 0.26 l of diisopropylethylamine (DIPEA) were mixed in a 2 l Schott bottle and added to the resin in the reactor. The reactor was stirred for 10 minutes, then filtering with suction was carried out. After the capping, the resin was washed 5 times in the following sequence: DMF (24 l), isopropanol (31.1 l), DMF (8 l), DMF (31.5 l), DMF (31.5 l). The reactor here was filled each time with the respective washing solvent, then stirring was carried out for 3 minutes and filtering with suction was carried out again.

5.4 Coupling of Fmoc-Leu-OH at Position 10

5.4.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 35 minutes; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.4.2 Coupling of Fmoc-Leu-OH 21 l of DMF were added to the reactor. Thereafter, 1.158 kg of Fmoc-Leu-OH were weighed in and 5.3 l of DMF were added. After complete dissolution, this solution was emptied into the reactor, followed by a solution of 502 g hydroxybenzotriazole hydrate (HOBt hydrate) in 2.2 l of DMF. Finally, 413 g of N,N-diisopropylcarbodiimide (DIC) were added to the reactor. The coupling time was 6-18 h. After coupling, the solvent was filtered off from the resin by suction and the capping was immediately continued.

5.4.3 Capping (According to the Invention)

The reactor was filled with 26.3 l of DMF. At the same time, 1.2 l of DMF, 0.53 l of acetic anhydride and 0.26 l of diisopropylethylamine (DIPEA) were mixed in a 2 l Schott bottle and added to the resin in the reactor. The reactor was stirred for 10 minutes, then filtering with suction was carried out. After the capping, the resin was washed 5 times in the following sequence: DMF (24 l), isopropanol (31.1 l), DMF (8 l), DMF (31.5 l), DMF (31.5 l). The reactor here was filled each time with the respective washing solvent, then stirring was carried out for 3 minutes and filtering with suction was carried out again.

5.5 Coupling of Fmoc-Gly-OH at Position 4

5.5.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 35 minutes; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.5.2 Coupling of Fmoc-Gly-OH 21 l of DMF were added to the reactor. Thereafter, 1.217 kg of Fmoc-Gly-OH were weighed in and 5.3 l of DMF were added. After complete dissolution, this solution was emptied into the reactor, followed by a solution of 627 g of hydroxybenzotriazole hydrate (HOBt hydrate) in 2.2 l of DMF. Finally, 517 g of N,N-diisopropylcarbodiimide (DIC) were added to the reactor. The coupling time was 6-18 h. After coupling, the solvent was filtered off from the resin by suction and the capping was immediately continued.

5.5.3 Capping (According to the Invention)

The reactor was filled with 26.3 l of DMF. At the same time, 1.2 l of DMF, 0.53 l of acetic anhydride and 0.26 l of diisopropylethylamine (DIPEA) were mixed in a 2 l Schott bottle and added to the resin in the reactor. The reactor was stirred for 10 minutes, then filtering with suction was carried out. After the capping, the resin was washed 5 times in the following sequence: DMF (24 l), isopropanol (31.1 l), DMF (8 l), DMF (31.5 l), DMF (31.5 l). The reactor here was filled each time with the respective washing solvent, then stirring was carried out for 3 minutes and filtering with suction was carried out again.

5.6 Coupling of Fmoc-Thr(tBu)-OH at Position 5

5.6.1 Fmoc Cleavage 7 l of DMF were added to the reactor, followed by a mixture of 7.9 l of piperidine in 16.6 l of DMF. This mixture was stirred for 5 minutes, then filtered with suction. This process was repeated and stirring was carried out for 35 minutes; then filtering with suction was carried out again. After the Fmoc cleavage, the resin was washed 7 times in the following sequence: DMF (31.1 l), DMF (31.1 l), isopropanol (31.1 l), DMF (31.1 l), DMF (8 l), DMF (31.1 l), DMF (31.1 l). The reactor here was filled each time with the respective washing solvent, then stirring was carried out for 3 minutes and filtering with suction was carried out again.

5.6.2 Coupling of Fmoc-Thr(tBu)-OH 21 l of DMF were added to the reactor. Thereafter, 1.628 kg of FmocThr(tBu)-OH were weighed in and 5.3 l of DMF were added. After complete dissolution, this solution was emptied into the reactor, followed by a solution of 627 g of hydroxybenzotriazole hydrate (HOBt hydrate) in 2.2 l of DMF. Finally, 517 g of N,N-diisopropylcarbodiimide (DIC) were added to the reactor. The coupling time was 6-18 h. After coupling, the solvent was filtered off from the resin by suction and the capping was immediately continued.

5.6.3 Capping

The reactor was filled with 10.5 l of DMF. At the same time, 15.8 l of DMF, 3.2 l of acetic anhydride and 1.6 l of diisopropylethylamine (DIPEA) were mixed in a mixing vessel and added to the resin in the reactor. The reactor was stirred for 20 minutes, then filtering with suction was carried out. After the capping, the resin was washed 5 times in the following sequence: DMF (24 l), isopropanol (31.1 l), DMT (8 l), DMF (31.5 l), DMF (31.5 l). The reactor here was filled each time with the respective washing solvent, then stirring was carried out for 3 minutes and filtering with suction was carried out again.

5.7 Results

The HPLC chromatogram of the crude product of the Lixisenatide synthesis with the capping method according to the invention at the positions Arg(20), Glu(17), Gln(13), Leu(10) and Gly(4), and capping in the other couplings as described under 5.6.3, is shown in FIGS. 6A-6C. The peaks with the impurities acetyl(20-44), acetyl(17-44), acetyl(13-44), acetyl(10-44) and acetyl(4-44)/acetyl(6-44) are indicated.

5.8 Comparison

The capping steps of all couplings, as described under 5.6.3, were carried out, leading to increased formation of the undesired erroneous sequences Ac(20-44), Ac(17-44), Ac(13-44), Ac(10-44) and Ac(4-44)/Ac(6-44). The HPLC chromatogram of a crude Lixisenatide from this test is shown in FIG. 6A.

By using a milder capping mixture (2% acetic anhydride/ 1% DIPEA in DMF for 10 minutes), it was possible to reduce the level of acetylated erroneous sequences of Ac(20-44), Ac(17-44), Ac(13-44), Ac(10-44) and Ac(4-44) in the crude product of Lixisenatide or eliminate them therefrom. Since a Lixisenatide crude product which was prepared by the capping according to the invention included the acetylated by-products Ac(17-44), Ac(13-44) and Ac(10-44) in particular in considerably reduced amounts, the purification of Lixisenatide was simplified. As a result, pooling of the fractions after the first preparative chromatography run of Lixisenatide gave more fractions which met the specification criteria and thus did not have to be discarded. This led to an improved yield.

EXAMPLE 6

Capping at 9 Specific Positions in the Synthesis of Lixisenatide

As discussed in Example 5, the use of "mild" capping conditions in the synthesis of lixisenatide at positions Arg (20), Glu(17), Gln(13), Leu(10) or/and Gly(4) could improve the profile of undesired by-products.

This Example describes the influence of capping conditions upon the formation of acetylated and non-acetylated by-products. Variations in the temperature (15° C., room temperature [20° C.-23° C.], 30° C.), capping duration and the ingredients of the capping composition were performed:
  no capping,
  mild capping conditions: 10 min capping with 2% acetic anhydride and 1% of DI PEA (diisopropylethylamine)
  "normal" capping conditions: 20 min capping with 10% acetic anhydride and 5% of DIPEA
  40 min capping with 10% acetic anhydride and 5% of DIPEA Capping conditions of the present invention are the "mild conditions". These conditions were used in Example 5. These conditions were found to be advantageous.

Figure 1:
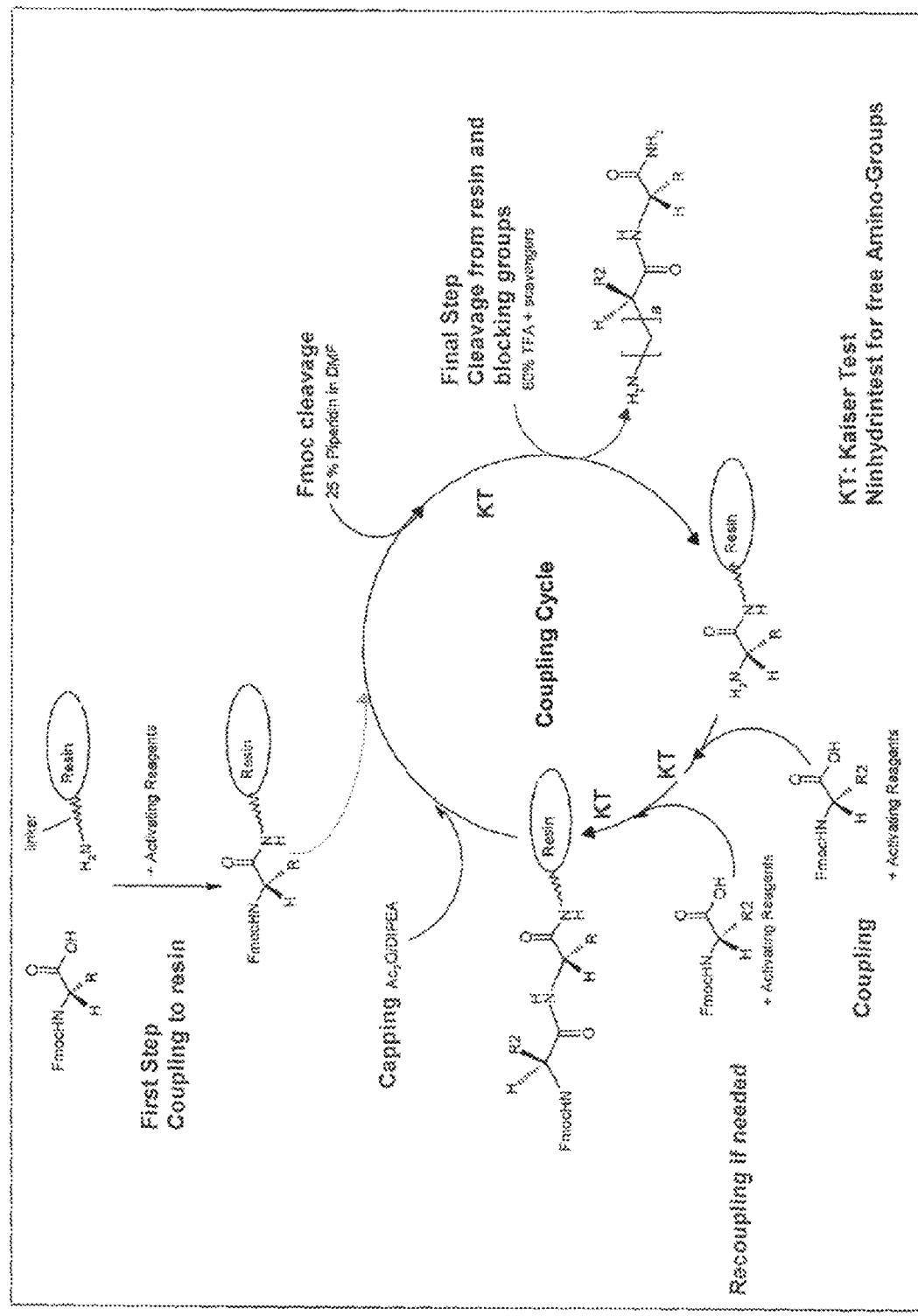
Figure 3:
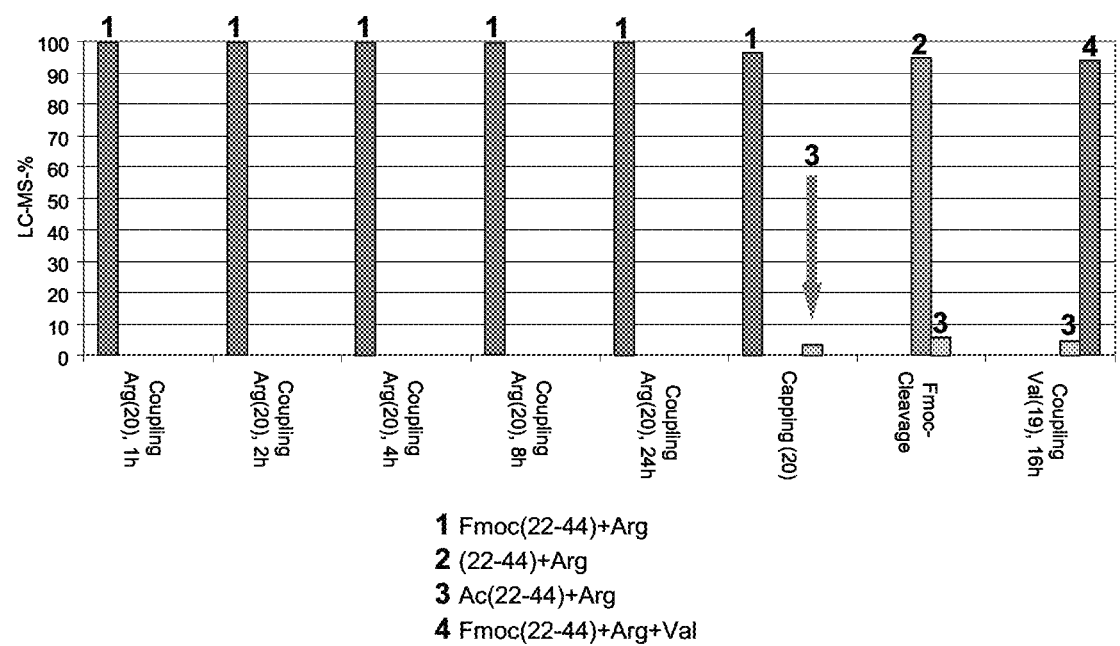
Figure 4:
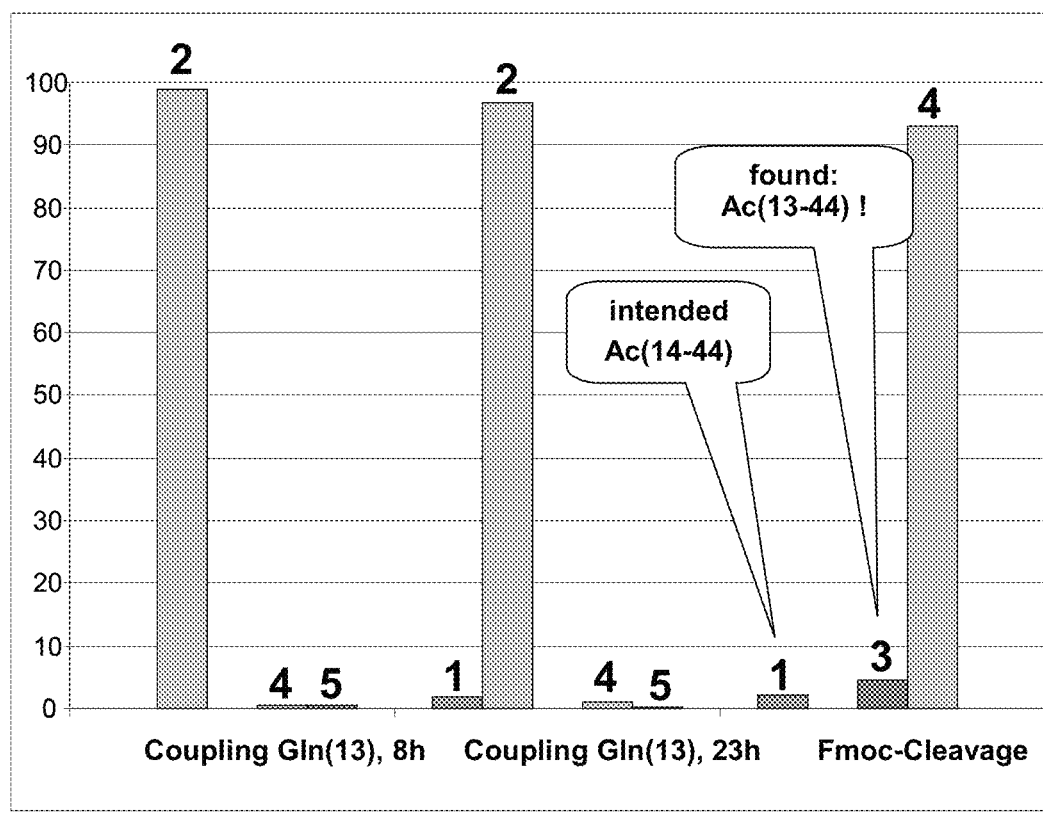
Figure 5:
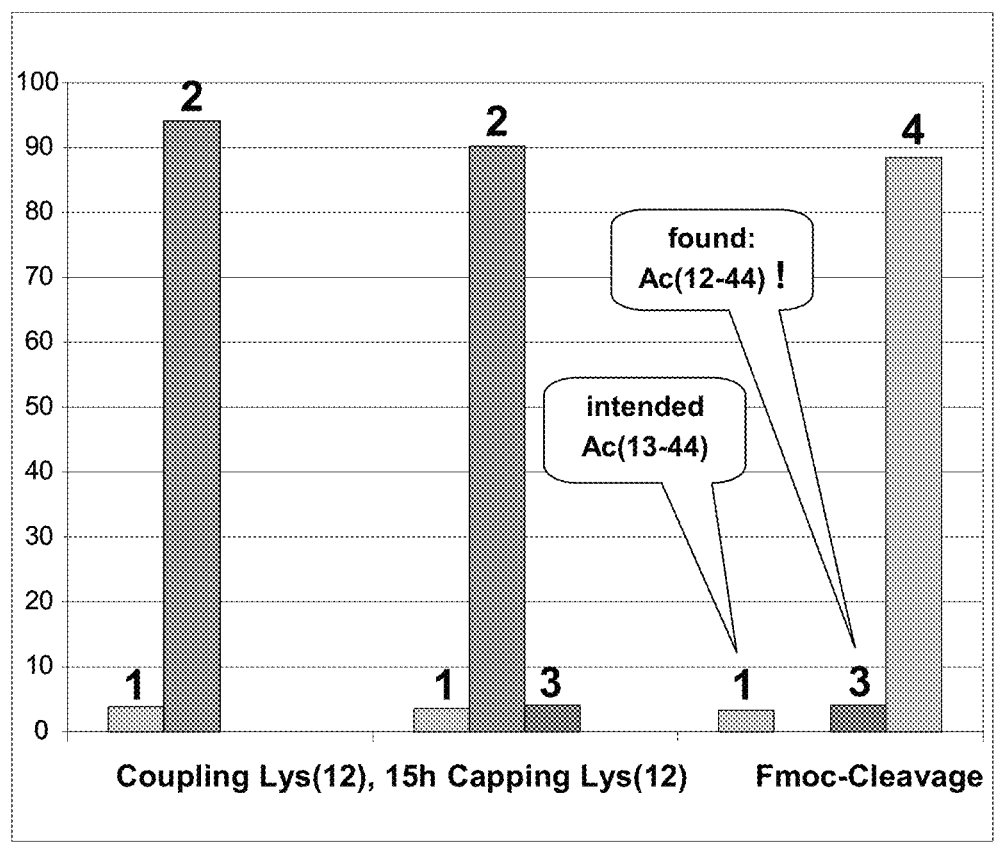
Figure 6A:
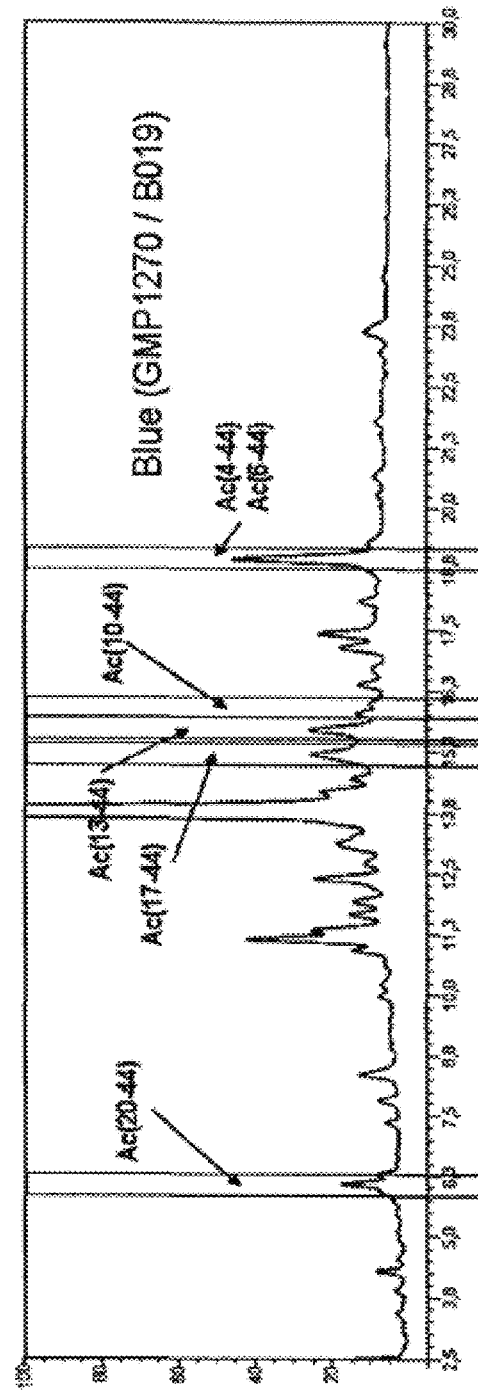
FIG. 6B shows a HPLC chromatogram of crude Lixisenatide, synthesized with the capping method according to the invention at the positions Arg(20), Glu(17), Gln(13), Leu (10) and Gly(4).
FIG. 6C shows the superimposition of the HPLC chromatograms from FIGS. 6A and B. It is apparent that the synthesis of Lixisenatide using the capping method according to the invention in batch operation led to a distinct reduction in the erroneous sequences Ac(20-44), Ac(17-44), Ac(13-44), Ac(10-44) and Ac(4-44)/Ac(6-44).
Figure 6B:
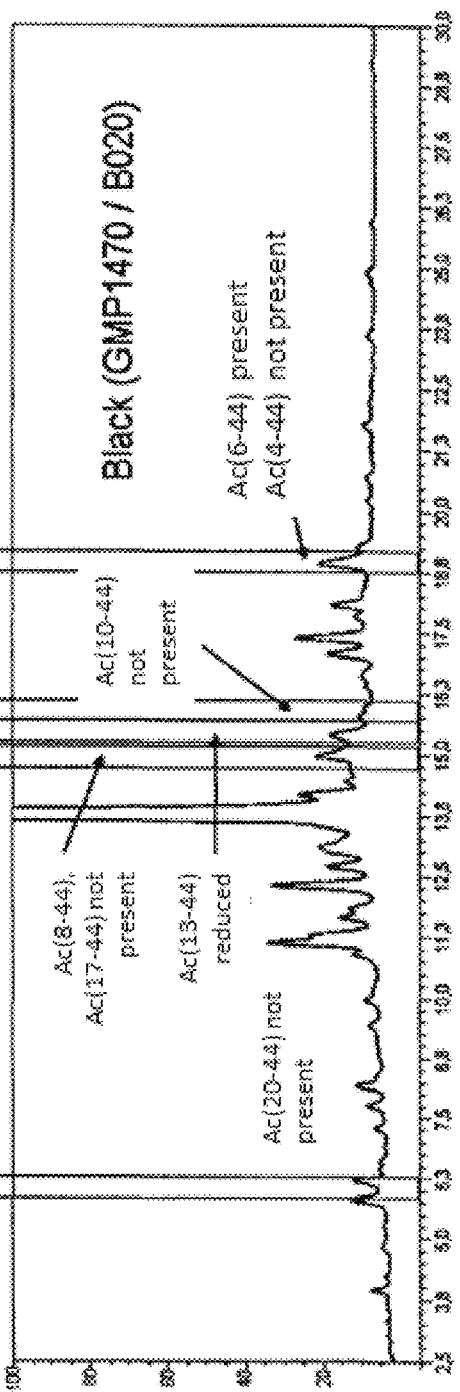
Figure 6C:
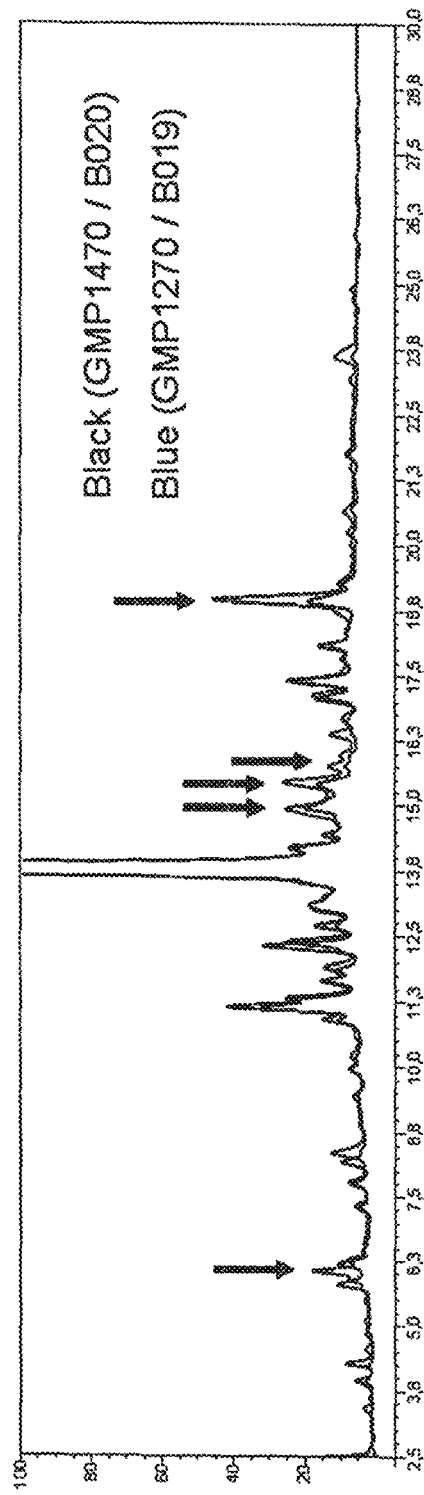
Figure 7:
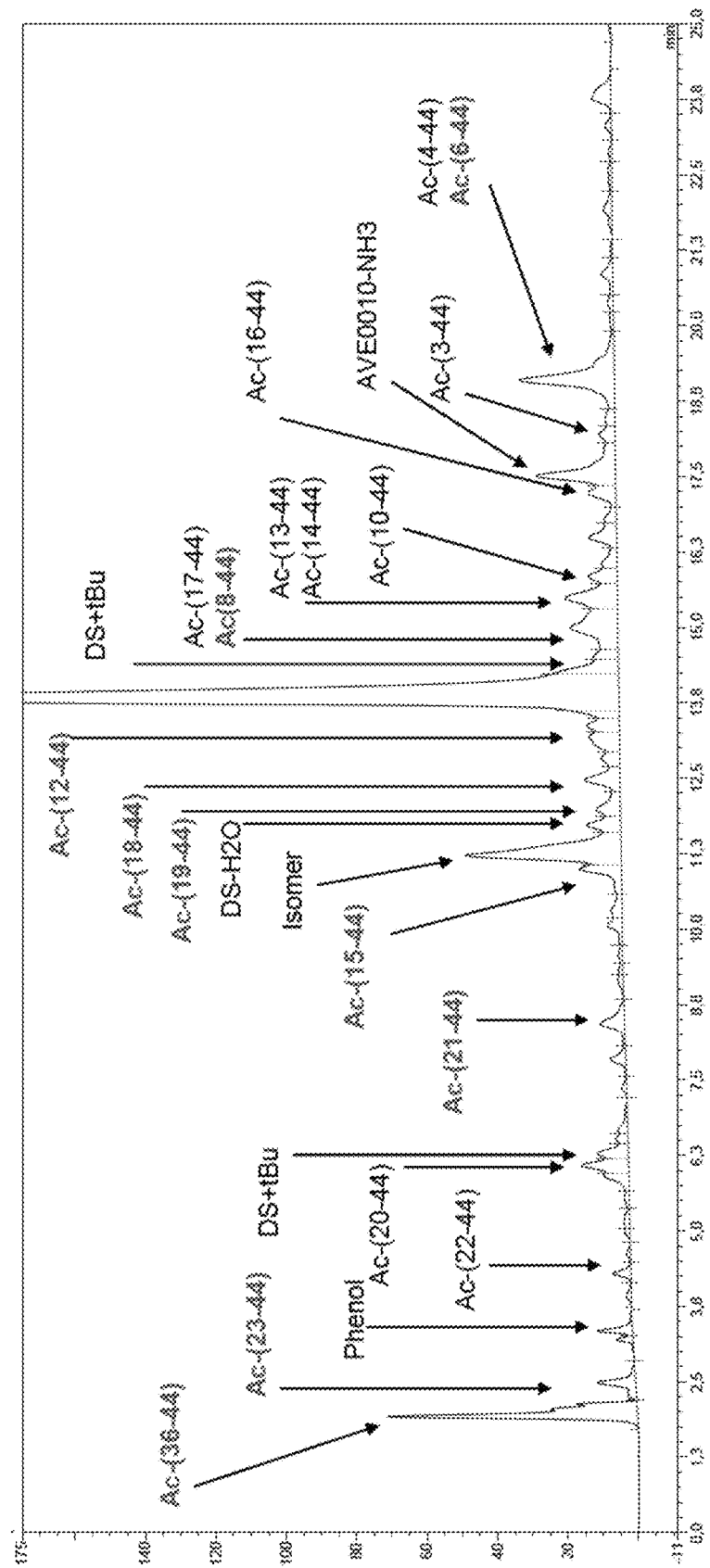

At the 9 positions selected in this Example, acetylated sequences are obtained at capping of the (N−1) position (FIG. 7). Additionally, undesired removal of the Fmoc group at the amino acid building block may occur during the capping step. The unprotected amino group may be acetylated by the capping reagent or capping composition. In this respect, improved capping conditions may avoid the undesired cleavage of the Fmoc group.

6.1 Capping at Position 36/35, after Coupling of the Dipeptide Building Block Pro-Pro, (36-44)

Peptide Fmoc-(36-44)-AVE0010 was produced by solid phase synthesis. The resin was dried in divided into 4 portions. Each portion underwent one of the four capping procedures described above at room temperature (20° C.-23° C.). Samples were dried, and the peptide was cleaved from the resin. This procedure was repeated, wherein capping was performed at 15° C. or 30° C.

In a total 12 peptide samples were obtained. The 12 peptide samples were analyzed with LCMS. Molecular weights were determined from the TIC (total ion current). The molecular weights of the following compounds were determined:

TABLE 7

| | |
|---|---|
| Ac(36-44) | can be formed by Fmoc cleavage during capping and subsequent acetylation (undesired by-product) |
| Fmoc(36-44) | desired product (main product) of solid phase synthesis |
| (36-44) | can be formed by Fmoc cleavage during capping, but no acetylation takes place (undesired by-product) |
| (38-44) | may be still present if coupling of the Fmoc-dipeptide building block was incomplete, but no acetylation takes place during the capping step (undesired by-product) |
| Ac(38-44) | desired capping product, may be formed by capping if coupling of the Fmoc-dipeptide building block was incomplete. |

Table 8 shows the content of products obtained after Fmoc-ProPro coupling and subsequence capping (% of total peptide content).

| | Ac(36-44) | Fmoc(36-44) | (36-44) | (38-44) | Ac(38-44) |
|---|---|---|---|---|---|
| Position 36/35 Pro-Pro, 15° C. | | | | | |
| without capping | 0.02 | 99.96 | 0 | 0.02 | 0 |
| 10 min, 2% Ac2O, 1% DIPEA (mild) | 0.37 | 99.6 | 0 | 0.03 | 0 |
| 20 min, 10% Ac2O, 5% DIPEA (normal) | 0.09 | 99.73 | 0 | 0.18 | 0 |
| 40 min, 10% Ac2O, 5% DIPEA | 0.4 | 99.57 | 0 | 0.02 | 0 |
| Position 36/35 Pro-Pro, RT | | | | | |
| without capping | 0.09 | 99.84 | 0 | 0 | 0.06 |
| 10 min, 2% Ac2O, 1% DIPEA (mild) | 0.47 | 99.47 | 0 | 0 | 0.06 |
| 20 min, 10% Ac2O, 5% DIPEA (normal) | 0.9 | 99.04 | 0 | 0 | 0.06 |
| 40 min, 10% Ac2O, 5% DIPEA | 1.52 | 98.42 | 0 | 0 | 0.05 |
| Position 36/35 Pro-Pro, 30° C. | | | | | |
| without capping | 0 | 100 | 0 | 0 | 0 |
| 10 min, 2% Ac2O, 1% DIPEA (mild) | 0.21 | 99.79 | 0 | 0 | 0 |
| 20 min, 10% Ac2O, 5% DIPEA (normal) | 0.66 | 99.34 | 0 | 0 | 0 |
| 40 min, 10% Ac2O, 5% DIPEA | 2.39 | 97.61 | 0 | 0 | 0 |

Figure 8:
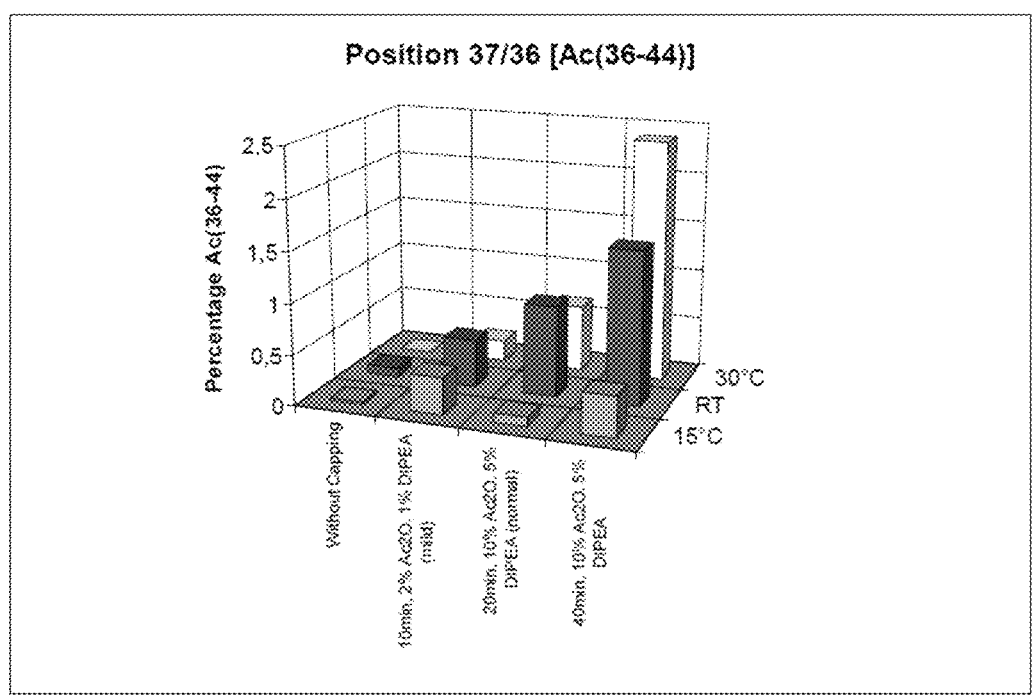

The results are described in FIG. 8. Compounds (36-44), (38-44) and Ac(38-44) were not found, or were found in small amounts. The amount of the undesired product Ac(36-44) increases with the strength of the capping cocktail and capping duration in most cases. The amount of this product increases with temperature.

6.2 Capping at Position 23, after Coupling of the Building Ile, (23-44)

The synthesis of Fmoc(23-44) was performed as described in section 6.1. Experiments at 15° C./30° C. and at room temperature were performed with different batches.

Table 9 shows the content of products obtained after Fmoc-Ile coupling and subsequence capping (% of total peptide content)

|  | Ac(23-44) | Fmoc(23-44) | (23-44) | (24-44) | Ac(24-44) |
|---|---|---|---|---|---|
| Position 23 Ile, 15° C. | | | | | |
| without capping | 0 | 99.7 | 0 | 0.16 | 0.14 |
| 10 min, 2% Ac2O, 1% DIPEA (mild) | 0 | 99.56 | 0.18 | 0.11 | 0.15 |
| 20 min, 10% Ac2O, 5% DIPEA (normal) | 0 | 99.57 | 0.2 | 0.11 | 0.13 |
| 40 min, 10% Ac2O, 5% DIPEA | 0 | 99.59 | 0.16 | 0.1 | 0.15 |
| Position 23 Ile, RT | | | | | |
| without capping | 0 | 99.81 | 0 | 0.19 | 0 |
| 10 min, 2% Ac2O, 1% DIPEA (mild) | 0.13 | 99.7 | 0 | 0.16 | 0 |
| 20 min, 10% Ac2O, 5% DIPEA (normal) | 0.26 | 99.54 | 0 | 0.2 | 0 |
| 40 min, 10% Ac2O, 5% DIPEA | 0.61 | 99.21 | 0 | 0.18 | 0 |
| Position 23 Ile, 30° C. | | | | | |
| without capping | 0 | 99.66 | 0 | 0.18 | 0.16 |
| 10 min, 2% Ac2O, 1% DIPEA (mild) | 0.1 | 99.38 | 0.19 | 0.16 | 0.17 |
| 20 min, 10% Ac2O, 5% DIPEA (normal) | 0.77 | 98.65 | 0.25 | 0.15 | 0.17 |
| 40 min, 10% Ac2O, 5% DIPEA | 1.43 | 98.15 | 0.16 | 0.12 | 0.14 |

Figure 9:
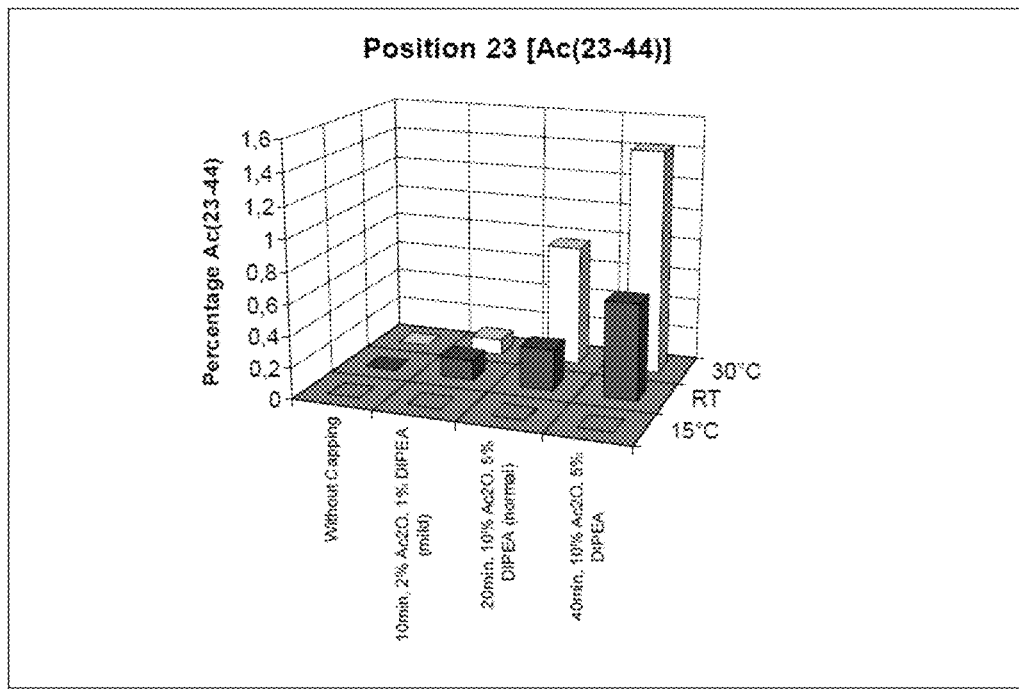

The results are described in FIG. 9. Depending upon the capping reagent at RT and 30° C., the content of undesired compound Ac(23-44) increases. "Normal" capping at 20° C. results in 0.26% of Ac(23-44). Prolongation of capping (40 min instead of 20 min) has a negative impact on the Ac(23-44) content.

Formation of the desired product Ac(24-44) is independent from the capping composition.

6.3 Capping at Position 21, after Coupling of the Building Block Leu, (21-44)

The synthesis of Fmoc(21-44) was performed as described in section 6.1. Experiments at 15° C./30° C. and at room temperature were performed with different batches.

Table 10 shows the content of products obtained after Fmoc-Leu coupling and subsequence capping (% of total peptide content)

|  | Ac(21-44) | Fmoc(21-44) | (21-44) | (22-44) | Ac(22-44) |
|---|---|---|---|---|---|
| Position 21 Leu, 15° C. | | | | | |
| without capping | 0 | 99.91 | 0 | 0 | 0.09 |
| 10 min, 2% Ac2O, 1% DIPEA (mild) | 0.03 | 99.78 | 0.07 | 0 | 0.12 |
| 20 min, 10% Ac2O, 5% DIPEA (normal) | 0.09 | 99.74 | 0.05 | 0 | 0.12 |
| 40 min, 10% Ac2O, 5% DIPEA | 0.36 | 99.48 | 0.03 | 0 | 0.13 |
| Position 21 Leu, RT | | | | | |
| without capping | 0 | 99.77 | 0 | 0.07 | 0.16 |
| 10 min, 2% Ac2O, 1% DIPEA (mild) | 0.06 | 99.64 | 0 | 0.14 | 0.16 |
| 20 min, 10% Ac2O, 5% DIPEA (normal) | 0.2 | 99.62 | 0 | 0.04 | 0.14 |
| 40 min, 10% Ac2O, 5% DIPEA | 0.46 | 99.34 | 0 | 0.04 | 0.16 |
| Position 21 Leu, 30° C. | | | | | |
| without capping | 0 | 99.86 | 0.04 | 0 | 0.11 |
| 10 min, 2% Ac2O, 1% DIPEA (mild) | 0.1 | 99.67 | 0.11 | 0 | 0.12 |
| 20 min, 10% Ac2O, 5% DIPEA (normal) | 0.86 | 98.95 | 0.06 | 0 | 0.13 |
| 40 min, 10% Ac2O, 5% DIPEA | 2.57 | 97.22 | 0.05 | 0 | 0.16 |

Figure 10:
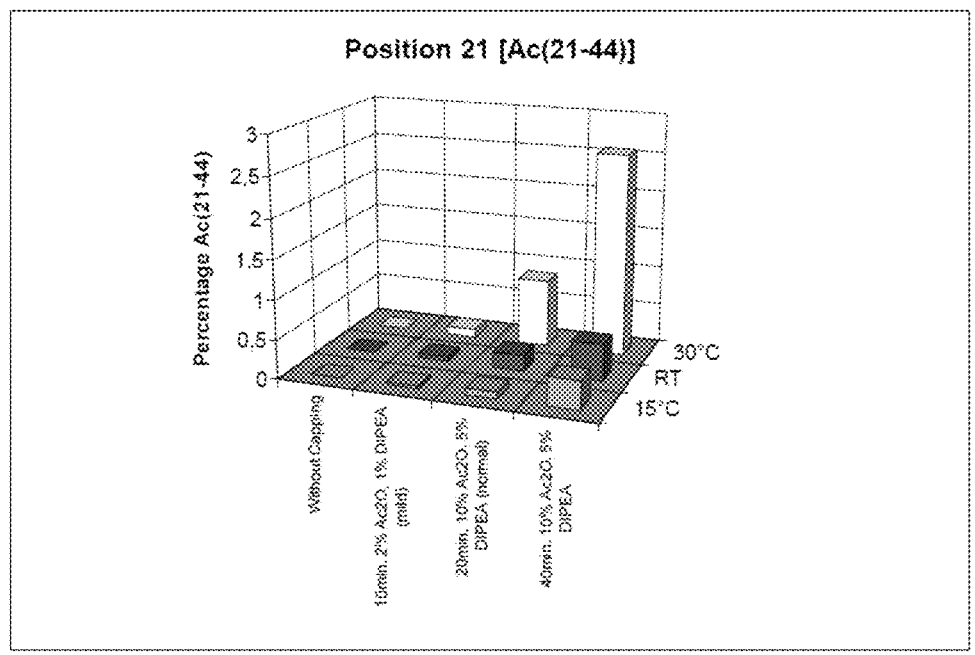

The results are described in FIG. 10. The content of undesired compound Ac(21-44) is largest at "40 min, 10% Ac2O, 5% DIPEA" at 15° C., RT and 30° C. The content of compound Ac(21-44) increases with temperature.

Formation of the desired compound Ac(22-44) is independent from the capping composition. Even without capping, this compound is formed.

6.4 Capping at Position 19, after Coupling of the Building Block Val, (19-44)

The synthesis of Fmoc(19-44) was performed as described in section 6.1. Experiments at 15° C./30° C. and at room temperature were performed with different batches.

Table 11 shows the content of products obtained after Fmoc-Val coupling and subsequence capping (% of total peptide content)

|  | Ac(19-44) | Fmoc(19-44) | (19-44) | (20-44) | Ac(20-44) |
|---|---|---|---|---|---|
| Position 19 Val, 15° C. | | | | | |
| without capping | 0 | 98.98 | 0.13 | 0.46 | 0.44 |
| 10 min, 2% Ac2O, 1% DIPEA (mild) | 0.11 | 98.79 | 0.44 | 0.25 | 0.4 |
| 20 min, 10% Ac2O, 5% DIPEA (normal) | 0.56 | 98.68 | 0.14 | 0.25 | 0.37 |
| 40 min, 10% Ac2O, 5% DIPEA | 1 | 98.17 | 0.09 | 0.23 | 0.51 |
| Position 19 Val, RT | | | | | |
| without capping | 0 | 99.61 | 0 | 0.23 | 0.16 |
| 10 min, 2% Ac2O, 1% DIPEA (mild) | 0.14 | 99.52 | 0 | 0.15 | 0.2 |
| 20 min, 10% Ac2O, 5% DIPEA (normal) | 0.43 | 99.23 | 0 | 0.17 | 0.17 |
| 40 min, 10% Ac2O, 5% DIPEA | 0.9 | 98.9 | 0 | 0 | 0.2 |
| Position 19 Val, 30° C. | | | | | |
| without capping | 0 | 99.16 | 0.08 | 0.4 | 0.36 |
| 10 min, 2% Ac2O, 1% DIPEA (mild) | 0.41 | 98.59 | 0.4 | 0.27 | 0.33 |
| 20 min, 10% Ac2O, 5% DIPEA (normal) | 2.3 | 96.89 | 0.14 | 0.22 | 0.45 |
| 40 min, 10% Ac2O, 5% DIPEA | 5.09 | 94.1 | 0.11 | 0.22 | 0.48 |

Figure 11:
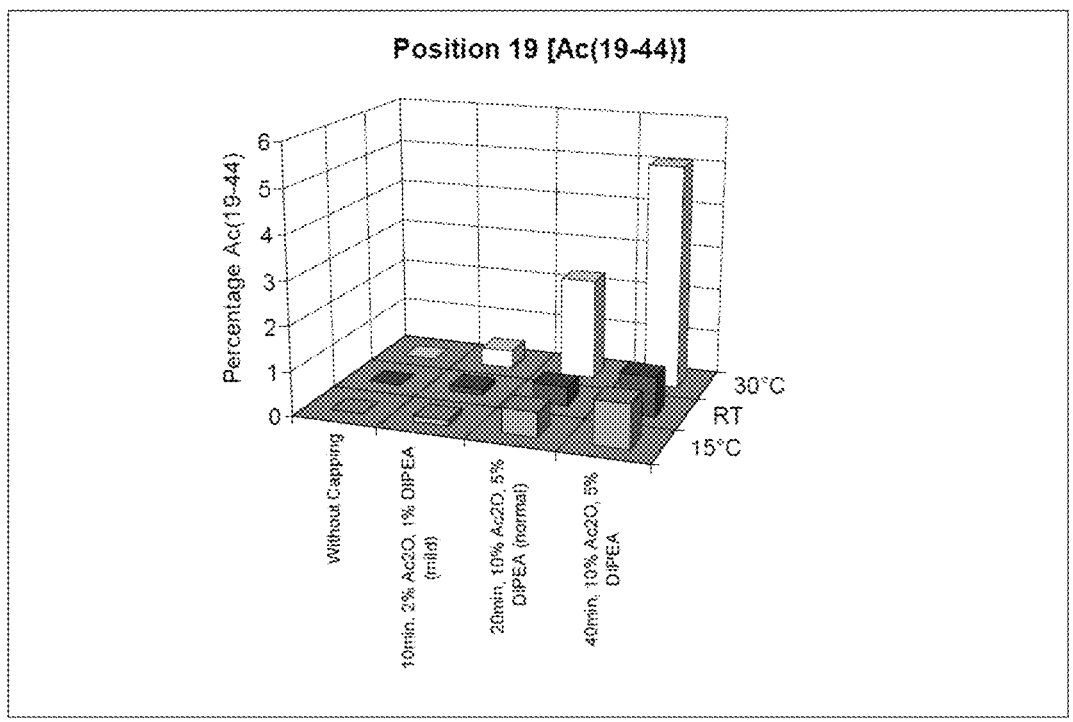

The results are described in FIG. 11. The content of compound Ac(19-44) is largest at "40 min, 10% Ac2O, 5% DIPEA" at 15° C., RT and 30° C. The content of compound Ac(19-44) increases with temperature.

Formation of the desired compound Ac(20-44) increases with the strength of the capping composition. The content of undesired (20-44) decreases with increasing strength of the capping composition.

6.5 Capping at Position 18, after Coupling of the Building Block Ala, (18-44)

The synthesis of Fmoc(18-44) was performed as described in section 6.1. Experiments at 15° C./30° C. and at room temperature were performed with different batches.

Table 12 shows the content of products obtained after Fmoc-Ala coupling and subsequence capping (% of total peptide content)

|  | Ac(18-44) | Fmoc(18-44) | (18-44) | (19-44) | Ac(19-44) |
|---|---|---|---|---|---|
| Position 18 Ala, 15° C. | | | | | |
| without capping | 0 | 98.77 | 0.48 | 0.33 | 0.42 |
| 10 min, 2% Ac2O, 1% DIPEA (mild) | 0.48 | 98.24 | 0.53 | 0.26 | 0.49 |
| 20 min, 10% Ac2O, 5% DIPEA (normal) | 0.76 | 98.18 | 0.27 | 0.2 | 0.59 |
| 40 min, 10% Ac2O, 5% DIPEA | 1.12 | 97.91 | 0.23 | 0.22 | 0.52 |
| Position 18 Ala, RT | | | | | |
| without capping | 0 | 99.63 | 0 | 0 | 0.37 |
| 10 min, 2% Ac2O, 1% DIPEA (mild) | 0.1 | 99.43 | 0.1 | 0 | 0.36 |
| 20 min, 10% Ac2O, 5% DIPEA (normal) | 0.77 | 98.69 | 0.18 | 0 | 0.36 |
| 40 min, 10% Ac2O, 5% DIPEA | 0.38 | 99.28 | 0 | 0 | 0.38 |
| Position 18 Ala, 30° C. | | | | | |
| without capping | 0 | 98.76 | 0.53 | 0.2 | 0.5 |
| 10 min, 2% Ac2O, 1% DIPEA (mild) | 0.92 | 98.07 | 0.32 | 0.11 | 0.58 |
| 20 min, 10% Ac2O, 5% DIPEA (normal) | 2.44 | 96.67 | 0.09 | 0.14 | 0.65 |
| 40 min, 10% Ac2O, 5% DIPEA | 6.33 | 92.73 | 0.05 | 0.14 | 0.73 |

Figure 12:
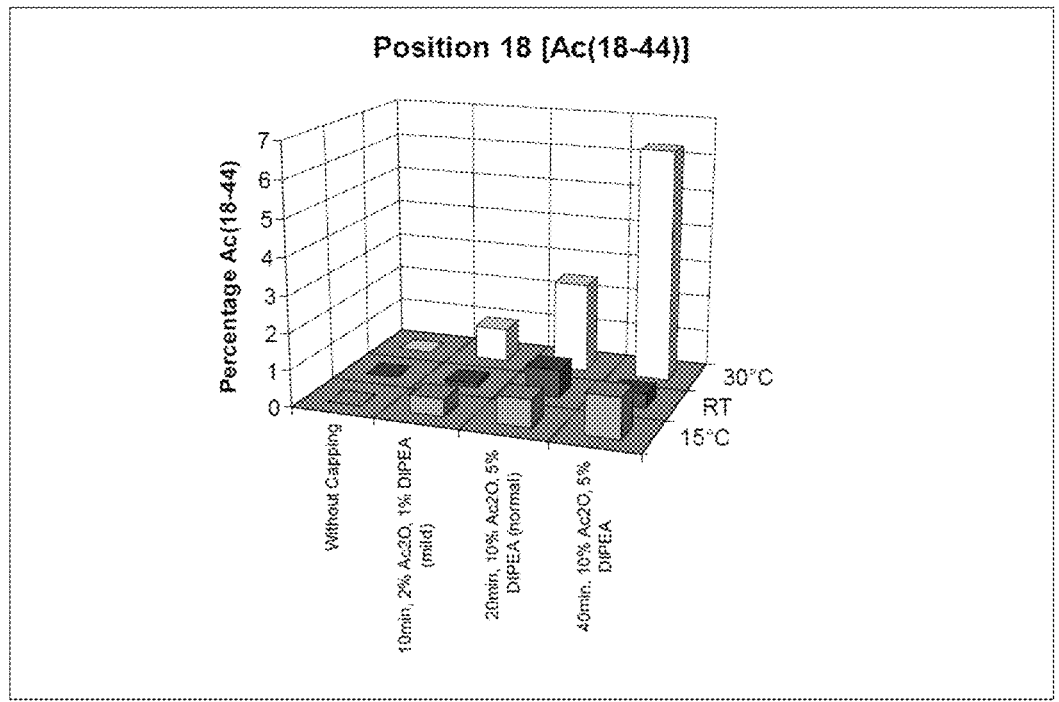

The results are described in FIG. 12. The content of undesired compound Ac(18-44) is largest at "40 min, 10% Ac2O, 5% DIPEA" at 15° C. and 30° C. The content of compound Ac(18-44) increases with temperature increase from 15° C. to 30° C.

Formation of the desired compound Ac(19-44) increases at 15° C. and 30° C. with the strength of the capping composition.

6.6 Capping at Position 15, after Coupling of the Building Block Glu (15-44)

The synthesis of Fmoc(15-44) was performed as described in section 6.1. Experiments at 15° C./30° C. and at room temperature were performed with different batches.

Table 13 shows the content of products obtained after Fmoc-Glu coupling and subsequence capping (% of total peptide content)

|  | Ac(15-44) | Fmoc(15-44) | (15-44) | (16-44) | Ac(16-44) |
|---|---|---|---|---|---|
| Position 15 Glu, 15° C. | | | | | |
| without capping | 0 | 99.28 | 0 | 0.59 | 0.13 |
| 10 min, 2% Ac2O, 1% DIPEA (mild) | 0.05 | 99.08 | 0.15 | 0.57 | 0.15 |
| 20 min, 10% Ac2O, 5% DIPEA (normal) | 0.19 | 99.08 | 0 | 0.58 | 0.15 |
| 40 min, 10% Ac2O, 5% DIPEA | 0.39 | 98.82 | 0 | 0.63 | 0.16 |
| Position 15 Glu, RT | | | | | |
| without capping | 0 | 99.72 | 0.12 | 0 | 0.17 |
| 10 min, 2% Ac2O, 1% DIPEA (mild) | 0.1 | 99.4 | 0.36 | 0 | 0.16 |
| 20 min, 10% Ac2O, 5% DIPEA (normal) | 0.42 | 99.13 | 0.2 | 0.04 | 0.21 |
| 40 min, 10% Ac2O, 5% DIPEA | 0.89 | 98.65 | 0.22 | 0.05 | 0.19 |
| Position 15 Glu, 30° C. | | | | | |
| without capping | 0 | 98.93 | 0 | 0.91 | 0.16 |
| 10 min, 2% Ac2O, 1% DIPEA (mild) | 0.17 | 98.7 | 0 | 0.95 | 0.18 |
| 20 min, 10% Ac2O, 5% DIPEA (normal) | 1.62 | 97.3 | 0 | 0.88 | 0.2 |
| 40 min, 10% Ac2O, 5% DIPEA | 3.24 | 95.63 | 0 | 0.94 | 0.19 |

Figure 13:
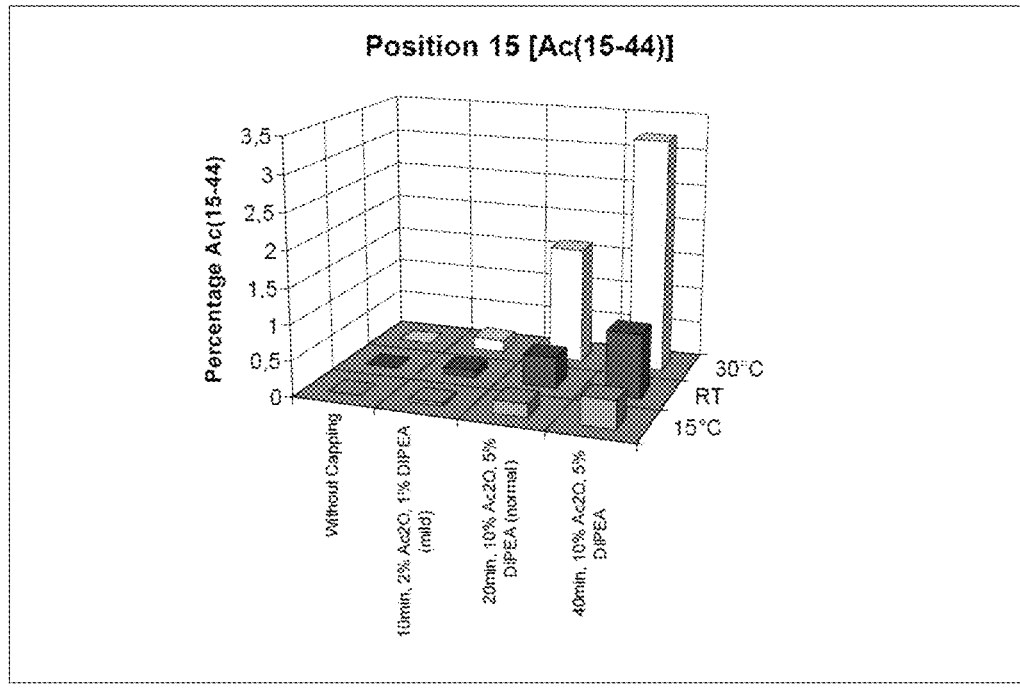

The results are described in FIG. 13. The content of undesired compound Ac(15-44) is largest at "40 min, 10% Ac2O, 5% DIPEA" at 15° C., RT and 30° C. The content of compound Ac(15-44) increases with temperature.

Formation of the desired compound Ac(16-44) is independent from the capping composition. Even without capping, this compound is formed.

6.7 Capping at Position 12, after Coupling of the Building Block Lys (12-44)

The synthesis of Fmoc(12-44) was performed as described in section 6.1. Experiments at 15° C./30° C. and at room temperature were performed with different batches.

Table 14 shows the content of products obtained after Fmoc-Lys coupling and subsequence capping (% of total peptide content)

|  | Ac(12-44) | Fmoc(12-44) | (12-44) | (13-44) | Ac(13-44) |
|---|---|---|---|---|---|
| Position 12 Lys, 15° C. | | | | | |
| without capping | 0 | 99.43 | 0.13 | 0 | 0.44 |
| 10 min, 2% Ac2O, 1% DIPEA (mild) | 0.15 | 99.25 | 0.17 | 0 | 0.43 |
| 20 min, 10% Ac2O, 5% DIPEA (normal) | 0.3 | 99.03 | 0.17 | 0 | 0.49 |
| 40 min, 10% Ac2O, 5% DIPEA | 0.55 | 98.88 | 0.16 | 0 | 0.41 |
| Position 12 Lys, RT | | | | | |
| without capping | 0 | 99.12 | 0 | 0.17 | 0.71 |
| 10 min, 2% Ac2O, 1% DIPEA (mild) | 0 | 99.29 | 0 | 0 | 0.71 |
| 20 min, 10% Ac2O, 5% DIPEA (normal) | 0.5 | 98.76 | 0 | 0 | 0.74 |
| 40 min, 10% Ac2O, 5% DIPEA | 1.12 | 98.15 | 0 | 0 | 0.73 |
| Position 12 Lys, 30° C. | | | | | |
| without capping | 0 | 99.41 | 0.15 | 0 | 0.44 |
| 10 min, 2% Ac2O, 1% DIPEA (mild) | 0.35 | 99.02 | 0.16 | 0 | 0.47 |
| 20 min, 10% Ac2O, 5% DIPEA (normal) | 1.55 | 97.89 | 0.14 | 0 | 0.41 |
| 40 min, 10% Ac2O, 5% DIPEA | 3.53 | 95.87 | 0.16 | 0 | 0.44 |

Figure 14:
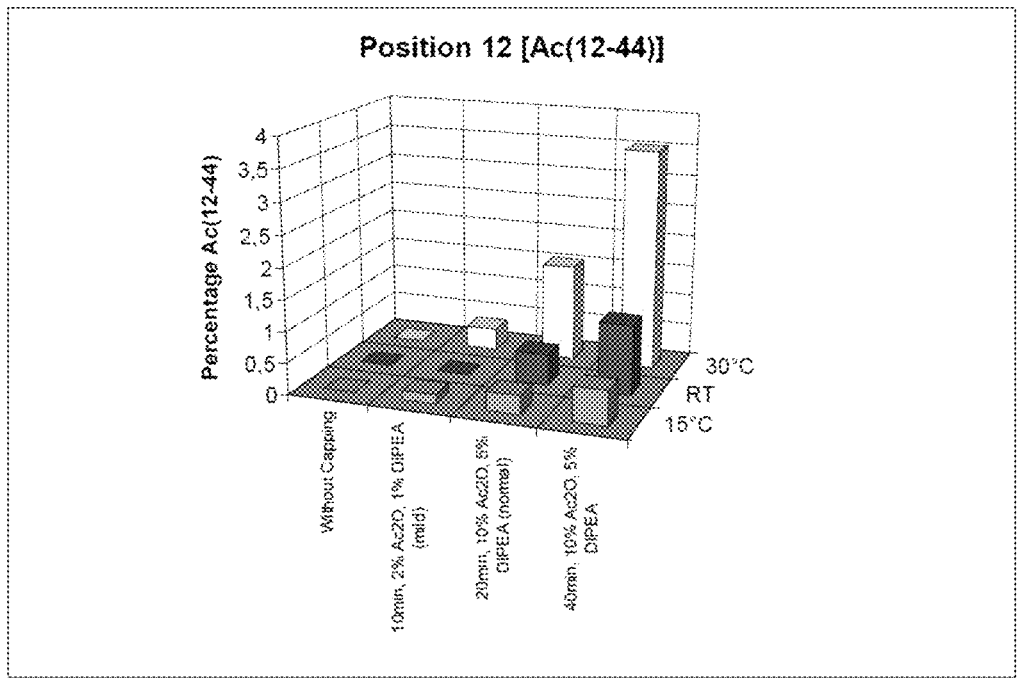

The results are described in FIG. 14. The content of undesired compound Ac(12-44) is largest at "40 min, 10% Ac2O, 5% DIPEA" at 15° C., RT and 30° C. The content of compound Ac(12-44) increases with temperature.

Formation of the desired compound Ac(13-44) is independent from the capping composition. Even without capping, this compound is formed.

6.8 Capping at Position 8, after Coupling of the Building Block Ser (8-44)

The synthesis of Fmoc(8-44) was performed as described in section 6.1. Experiments at 15° C., RT and 30° C. were performed with the same batch.

Table 15 shows the content of products obtained after Fmoc-Ser coupling and subsequence capping (% of total peptide content)

Figure 16:
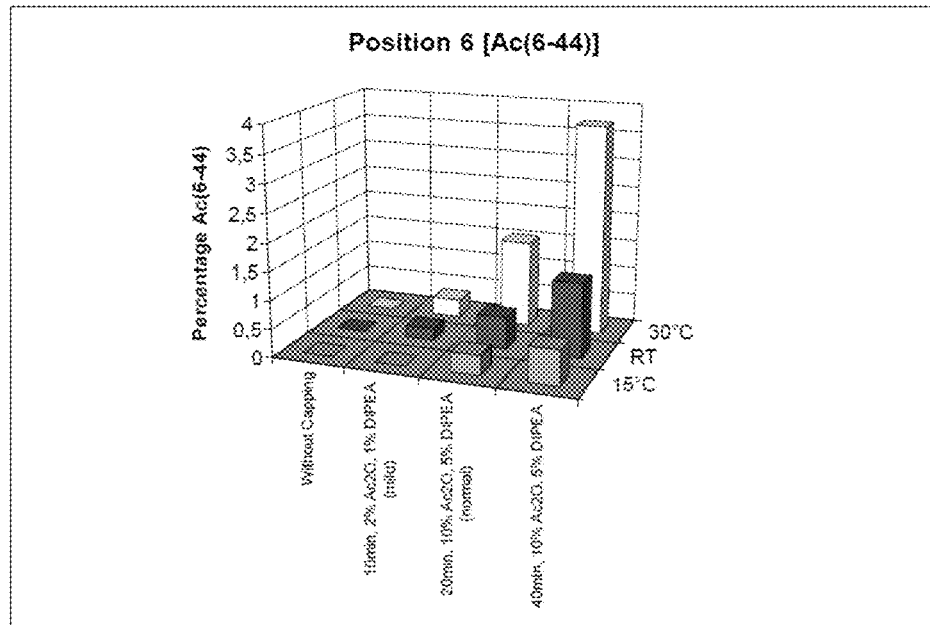

The results are described in FIG. 16. The content of undesired compound Ac(6-44) is largest at "40 min, 10% Ac2O, 5% DIPEA" at 15° C., RT and 30° C. The content of compound Ac(6-44) increases with temperature.

Formation of the desired compound Ac(7-44) is independent from the capping composition. Even without capping, this compound is formed.

Temperature has only slight influence on formation of the desired compound Ac(7-44). The content of undesired (7-44) decreases with increasing strength of the capping composition.

6.10 Summary

Undesired formation of Ac(X-44)-compound strongly depends upon the capping duration, the capping composition and the capping temperature. With increasing capping dura-

|  | Ac(8-44) | Fmoc(8-44) | (8-44) | (9-44) | Ac(9-44) |
|---|---|---|---|---|---|
| Position 8 Ser, 15° C. | | | | | |
| without capping | 0 | 100 | 0 | 0 | 0 |
| 10 min, 2% Ac2O, 1% DIPEA (mild) | 0 | 99.79 | 0 | 0 | 0.21 |
| 20 min, 10% Ac2O, 5% DIPEA (normal) | 0.29 | 99.53 | 0 | 0 | 0.18 |
| 40 min, 10% Ac2O, 5% DIPEA | 1.08 | 98.72 | 0 | 0 | 0.21 |
| Position 8 Ser, RT | | | | | |
| without capping | 0 | 99.67 | 0 | 0.18 | 0.16 |
| 10 min, 2% Ac2O, 1% DIPEA (mild) | 0.22 | 99.78 | 0 | 0 | 0 |
| 20 min, 10% Ac2O, 5% DIPEA (normal) | 1.12 | 98.88 | 0 | 0 | 0 |
| 40 min, 10% Ac2O, 5% DIPEA | 2.1 | 97.9 | 0 | 0 | 0 |
| Position 8 Ser, 30° C. | | | | | |
| without capping | 0 | 100 | 0 | 0 | 0 |
| 10 min, 2% Ac2O, 1% DIPEA (mild) | 0.29 | 99.27 | 0.27 | 0 | 0.18 |
| 20 min, 10% Ac2O, 5% DIPEA (normal) | 2.1 | 97.8 | 0 | 0 | 0.1 |
| 40 min, 10% Ac2O, 5% DIPEA | 5.02 | 94.74 | 0 | 0 | 0.24 |

Figure 15:
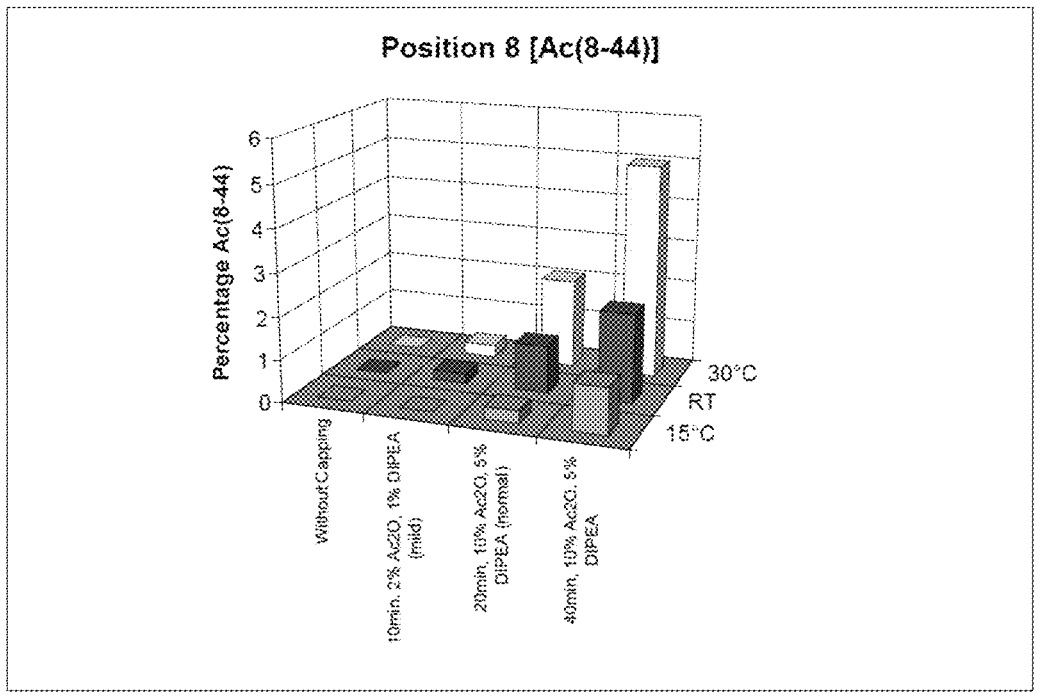

The results are described in FIG. 15. The content of undesired compound Ac(8-44) is largest at "40 min, 10% Ac2O, 5% DIPEA" at 15° C., RT and 30° C. The content of compound Ac(8-44) increases with temperature.

6.9 Capping at Position 6, after Coupling of the Building Block Phe (6-44)

The synthesis of Fmoc(86-44) was performed as described in section 6.1. Experiments at 15° C., RT and 30° C. were performed with the same batch.

Table 16 shows the content of products obtained after Fmoc-Phe coupling and subsequence capping (% of total peptide content)

tion, increasing capping temperature, and increased content of acetic anhydride and DIPEA in the capping composition the content of undesired Ac(X-44) compound increases.

6.11 Capping Under "Normal" Conditions, Depending Upon Temperature.

Figure 17:
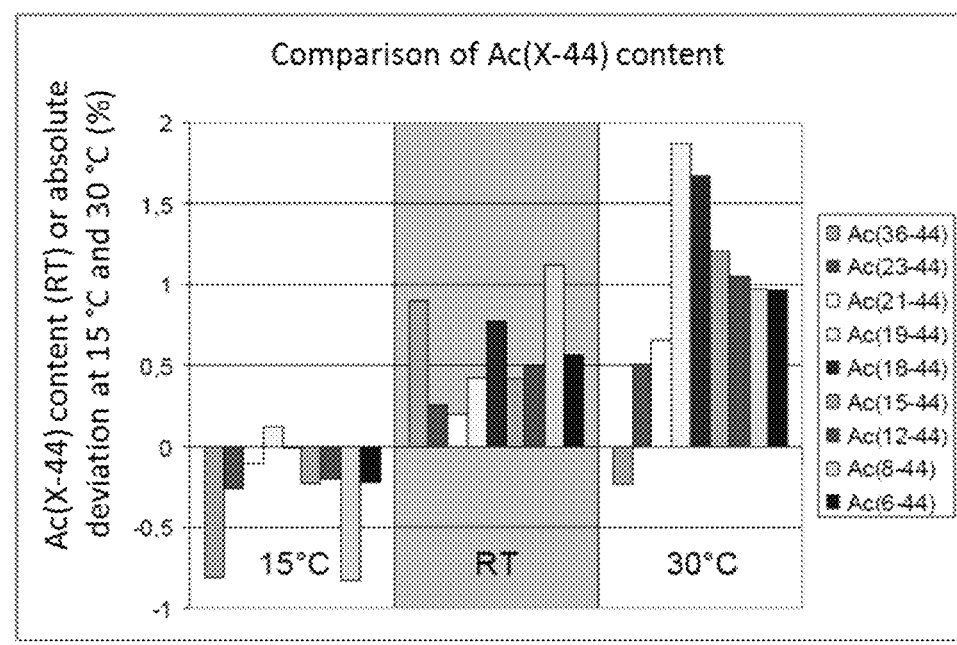
Figure 18:
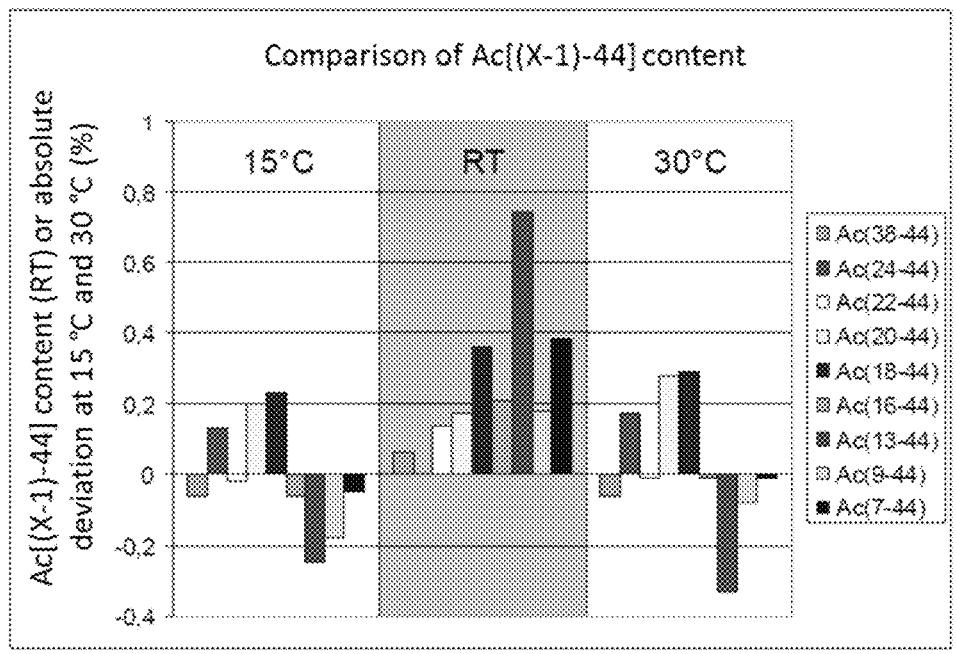

FIGS. 17 and 18 summarize the data obtained in capping at different temperatures at the 9 positions in the synthesis of Lixisenatide under "normal" conditions "20 min, 10% Ac2O, 5% DIPEA", as described in this Example.

FIG. 17 shows a comparison of GMP capping of Ac(X-44), depending on reaction temperature. Values given for

|  | Ac(6-44) | Fmoc(6-44) | (6-44) | (7-44) | Ac(7-44) |
|---|---|---|---|---|---|
| Position 6 Phe, 15° C. | | | | | |
| without capping | 0 | 99.21 | 0 | 0.38 | 0.41 |
| 10 min, 2% Ac2O, 1% DIPEA (mild) | 0 | 99 | 0.39 | 0.28 | 0.34 |
| 20 min, 10% Ac2O, 5% DIPEA (normal) | 0.35 | 98.73 | 0.32 | 0.26 | 0.33 |
| 40 min, 10% Ac2O, 5% DIPEA | 0.62 | 98.6 | 0.3 | 0.18 | 0.3 |
| Position 6 Phe, RT | | | | | |
| without capping | 0 | 99.24 | 0 | 0.39 | 0.37 |
| 10 min, 2% Ac2O, 1% DIPEA (mild) | 0.2 | 98.68 | 0.6 | 0.25 | 0.28 |
| 20 min, 10% Ac2O, 5% DIPEA (normal) | 0.57 | 98.49 | 0.31 | 0.25 | 0.38 |
| 40 min, 10% Ac2O, 5% DIPEA | 1.32 | 97.9 | 0.33 | 0.2 | 0.24 |
| Position 6 Phe, 30° C. | | | | | |
| without capping | 0 | 99.24 | 0 | 0.43 | 0.33 |
| 10 min, 2% Ac2O, 1% DIPEA (mild) | 0.33 | 98.36 | 0.55 | 0.29 | 0.46 |
| 20 min, 10% Ac2O, 5% DIPEA (normal) | 1.54 | 97.42 | 0.37 | 0.3 | 0.37 |
| 40 min, 10% Ac2O, 5% DIPEA | 3.73 | 95.91 | 0 | 0 | 0.36 |

15° C. and 30° C. are positive and negative deviations from "room temperature" values (grey area).

The formation of undesired product Ac(X-44) is 0.5% in 5 of 9 positions, in 3 positions between 0.5% and 1%, and in only one position >1%. A large increase is observed at 30° C., while at 15° C., formation of Ac(X-44) slightly decreases.

This means that GMP capping "20 min, 10% Ac2O, 5% DIPEA" can be performed at different positions between 15° C. and room temperature, which can be 20-23° C.

FIG. 18 shows a comparison of GMP capping of Ac[(X-1)-44], depending on reaction temperature. Values given for 15° C. and 30° C. are positive and negative deviations from "room temperature" values (grey area)

Regarding the desired formation of the Ac[(X-1)-44] compounds at RT, the deviation at 15° C. is between +0.23 und −0.25%. At 30° C., the deviation is between +0.29 und −0.33%. Formation of the desired capping product Ac[(X-1)-44] is thus less dependent upon the temperature than the undesired formation of Ac(X-44).

At 15° C. and 30° C., negative deviations of the content of desired compound Ac[(X-1)-44] are observed in view of capping at room temperature. This means that capping with "normal" conditions should be performed at room temperature.

6.12 Capping with Different Capping Compositions at Room Temperature.

Figure 19:
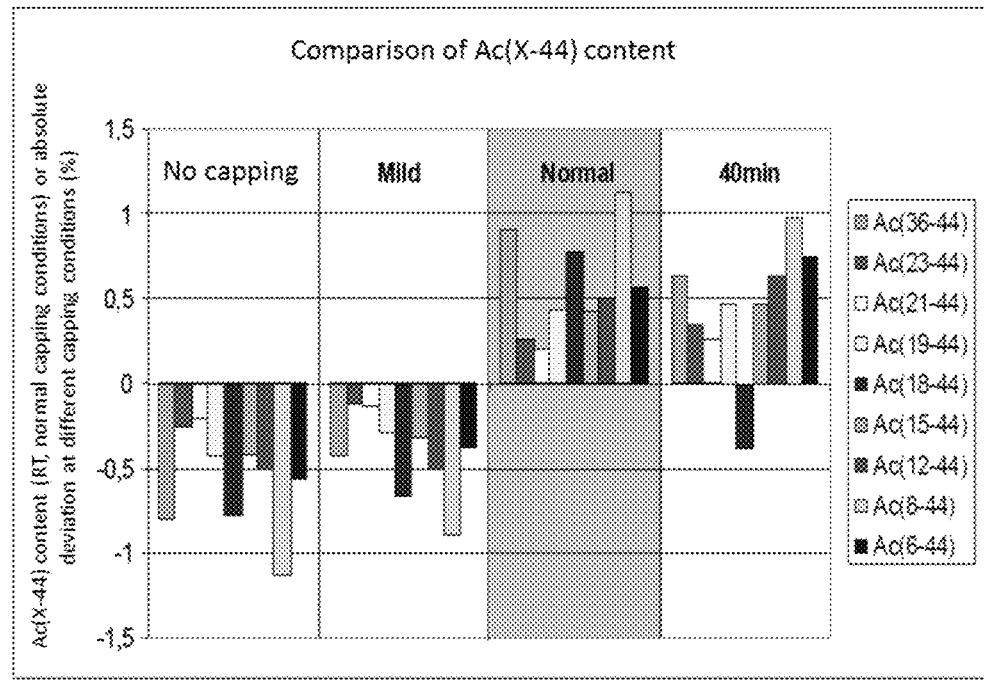
Figure 20:
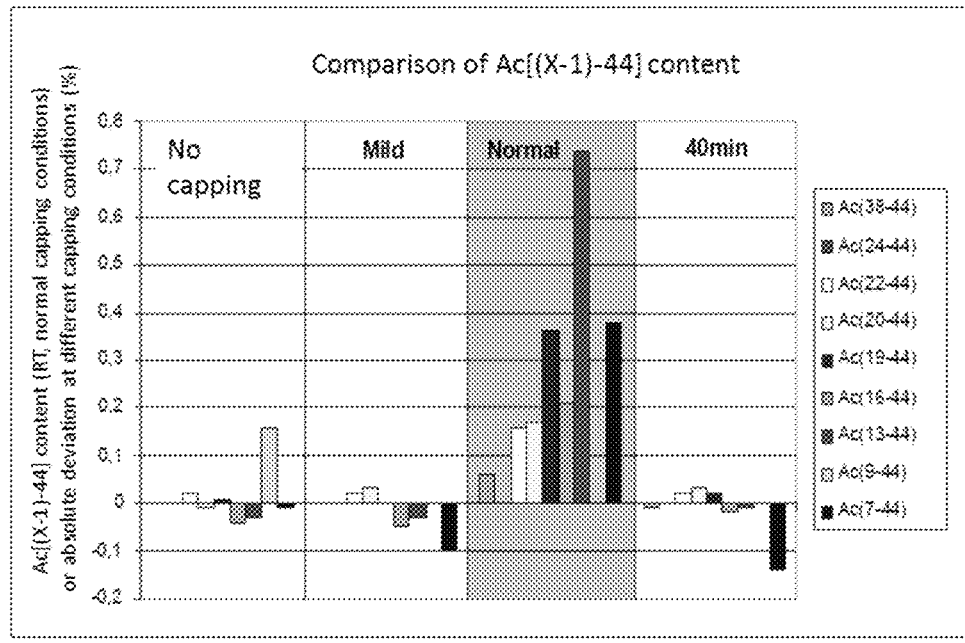

FIGS. 19 and 20 summarize the data obtained in capping with different capping compositions at room temperature at the 9 positions in the synthesis of lixisenatide, as described in this Example.

FIG. 19 shows a comparison of Ac(X-44) content, depending upon the capping composition at room temperature. Values given for "no capping", "mild" and "40 min" conditions are positive and negative deviations from "normal capping" values (grey area).

Formation of undesired product Ac(X-44) under "20 min, 10% Ac2O, 5% DIPEA" and "40 min, 10% Ac2O, 5% DIPEA" is largest. Formation of Ac(X-44) under "normal" conditions (40 min, 10% Ac2O, 5% DIPEA) is between 0.2% and 1.12%. A strong decrease is observed at mild capping conditions.

FIG. 20 shows a comparison of Ac[(X-1)-44] content, depending upon the capping composition at room temperature. Values given for "no capping", "mild" and "40 min" are positive and negative deviations from "normal capping" values (grey area).

The formation of the desired product Ac[(X-1)-44] at the conditions "no capping", "mild" and "40 min" is within −0.14% and +0.16% in view of the "normal" conditions.

In particular, under "mild" conditions (10 min, 2% Ac2O, 1% DIPEA) of the invention, sufficient capping can be achieved in the synthesis of lixisenatide.

In summary, mild capping conditions, in particular capping for 10 min with 2% Ac2O and 1% DIPEA in a solvent, are advantageous in the solid phase synthesis of lixisenatide, as described herein.

If capping is omitted after coupling at certain amino acid positions, undesired by-products comprising an incomplete amino acid sequence and being present in small amount, may be difficult to remove during the purification process.

EXAMPLE 7

Cleavage of Lixisenatide from the Solid Phase

This example relates to the cleavage according to the invention of Lixisenatide from a solid phase. A solid phase (Rink resin) was provided, to which the peptide Lixisenatide was bonded. The peptide was synthesized on the resin by stepwise coupling of amino acid units.

As comparative test, a cleavage according to the prior art (King et al., Int. J. Peptide Protein Res. 1990, 36: 255-266) was carried out.

The cleavage method according to the invention is distinguished from the method of the prior art by the following changes:

Reaction temperature from 20° C. to 26° C.

Number of components in the cleavage mixture reduced from 5 to 2 constituents, combined with increase in the ratio of resin to cleavage mixture used.

TABLE 17

Comparison of the cleavage method according to the invention and the cleavage according to the prior art. The differences are indicated in bold/underlined.

| Comparative process (prior art) | Method according to the invention |
|---|---|
| Cleavage mixture [g or ml/g "peptide on resin"]: <br>a) 0.5 g phenol <br>b) 0.5 ml thioanisole <br>c) 0.25 ml 1,2-ethanedithiol <br>d) 0.5 ml water <br>e) 8.25 ml TFA <br>("King's cocktail") | Cleavage mixture [ml/g "peptide on resin"]: <br>a) 0.25 ml 1,2-ethanedithiol <br>b) 8.25 ml TFA |
| Cleavage mixture is cooled to 5-10° C. and added to Lixisenatide-resin(1-44) | Cleavage mixture is cooled to 5-10° C. and added to Lixisenatide-resin(1-44) |
| Reaction mixture heated to 20° C. and stirred for 4 h | Reaction mixture heated to 26° C. and stirred for 4 h |
| Reaction mixture filtered | Reaction mixture filtered |
| Subsequent cleavage | Subsequent cleavage |
| The resin filtered off is added to TFA (10 ml per g of resin), stirred for 1 h and the resin is filtered off | The resin filtered off is added to TFA (10 ml per g of resin), stirred for 1 h and the resin is filtered off |
| Filtrate purified and solution concentrated by distillation under reduced pressure at 35-40° C. to at least ¹/₁₆th of the original volume. | Filtrate purified and solution concentrated by distillation under reduced pressure at 35-40° C. to at least ¹/₁₆th of the original volume. |
| Crude Lixisenatide precipitated by addition of the concentrate to 6 times the volume of | Crude Lixisenatide precipitated by addition of the concentrate to 6 times the volume of |

TABLE 17-continued

Comparison of the cleavage method according to the invention and the cleavage according to the prior art. The differences are indicated in bold/underlined.

| Comparative process (prior art) | Method according to the invention |
| --- | --- |
| DIPE | DIPE |
| The precipitate is resuspended twice in ethyl acetate and filtered off. | The precipitate is resuspended twice in ethyl acetate and filtered off. |
| The precipitate is dried and the crude Lixisenatide is isolated. | The precipitate is dried and the crude Lixisenatide is isolated. |

By using the cleavage according to the invention, compared to the cleavage according to the prior art, it was possible to increase the yields of the crude Lixisenatide by approximately 5% (from 20% to 25%), while the impurities profile was only slightly altered.

The method of this example is suitable for scale-up to the pilot-plant and production scale.

Table 18 summarizes the results obtained in the comparative process (see Table 17). Three different batches 2E002, 2B008 and 2B006 of lixisenatide-resin (1-44) were used. Means and standard deviation are calculated for each batch separately. Comparison between different cleavage conditions should be made in tests using the same batch of lixisenatide-resin (1-44). In different batches, the solid phase synthesis may have an impact on the yield. If not otherwise indicated, 10 g of lixisenatide-resin(1-44) were used as starting material.

TABLE 18

Content of lixisenatide in the resin, and yield of lixisenatide after cleavage of lixisenatide from the resin under standard conditions (comparative process, see Table 17).

| Number of experiment | Batch of lixisenatide-resin(1-44) | Output weight [g] | Content [%] | Yield [%] |
| --- | --- | --- | --- | --- |
| Batch 2E002 | | | | |
| 71002-002 | 2E002 | 2.60 | 22.9 | 10.2 |
| 71002-003 | 2E002 | 3.36 | 23.1 | 13.4 |
| 71002-012 | 2E002 | 1.88 | 20.3 | 6.6 |
| separate subsequent cleavage | | 0.77 | 25.0 | 3.3 |
| 70609-068 | 2E002 | 3.01 | 21.5 | 11.1 |
| 71002-035 | 2E002 | 3.08 | 16.3 | 8.6 |
| 71002-036 | 2E002 | 3.07 | 16.3 | 8.6 |
| 70586-043 | 2E002 | 2.40 | 24.3 | 10.1 |
| 71003-003 | 2E002 | 2.50 | 24.0 | 10.3 |
| Mean ± standard deviation | | | | 10.3 ± 1.5 |
| Batch 2B008 | | | | |
| 70586-052 | 2B008 | 2.84 | 26.9 | 14.7 |
| 71001-006 | 2B008 | 3.03 | 20.0 | 11.7 |
| 71002-048 | 2B008 | 2.89 | 22.8 | 12.7 |
| 71001-016 | 2B008 | 3.41 | 21.6 | 14.2 |
| Mean ± standard deviation | | | | 13.4 ± 1.4 |
| Batch 2B006 | | | | |
| 70586-056 | 2B006 | 3.02 | 25.0 | 14.3 |

7.1 Cleavage Yield Depending Upon the Cleavage Temperature Between 20° C. and 35° C.

Cleavage from the lixisenatide-resin(1-44) was performed under standard conditions (comparative process, see Table 17) for 4 h.

TABLE 19

Cleavage yield depending upon temperature

| Number of experiment | Batch of lixisenatide-resin(1-44) | Temperature [° C.] | Duration [h] | Yield [%] |
| --- | --- | --- | --- | --- |
| Standard | 2E002 | 20 | 4 | 10.3 ± 1.5 |
| 70586-050 | 2E002 | 23 | 4 | 11.7 |
| 70586-044 | 2E002 | 26 | 4 | 14.8 |
| 70586-046 | 2E002 | 30 | 4 | 14.2 |
| 70586-049 | 2E002 | 35 | 4 | 12.4 |

Results: The yield of lixisenatide after cleavage under standard conditions increases with increasing temperature until the optimum of about 26° C. Surprisingly, an increase of temperature from 23° C. to 26° C. results in a significant increase in yield.

7.2 Cleavage Yield Depending Upon the Cleavage Duration

Cleavage from the lixisenatide-resin(1-44) was performed under standard conditions (comparative process, see Table 17) at 20° C.

TABLE 20

Cleavage yield depending upon the cleavage duration

| Number of experiment | Batch of lixisenatide-resin(1-44) | Temperature [° C.] | Duration [h] | Yield [%] |
| --- | --- | --- | --- | --- |
| Standard | 2E002 | 20 | 4 | 10.3 ± 1.5 |
| 71002-037 | 2E002 | 20 | 6 | 11.3 |
| 71002-038 | 2E002 | 20 | 8 | 13.4 |
| 70586-037, 71003-002, 71003-004 | 2E002 | 20 | 12 | 13.1 ± 0.9 |

Results: The yield of lixisenatide increases with increased cleavage duration. A maximum yield is reached after about 8 h cleavage.

7.3 Cleavage Yield Depending Upon the Temperature at Cleavage Duration of 12 h Cleavage from the lixisenatide-resin(1-44) was performed under standard conditions (comparative process, see Table 17) for 4 h.

TABLE 21

Cleavage yield depending upon the temperature at cleavage duration of 12 h

| Number of experiment | Batch of lixisenatide-resin(1-44) | Temperature [° C.] | Duration [h] | Yield [%] |
| --- | --- | --- | --- | --- |
| 70586-040 | 2E002 | 17 | 12 | 10.7 |
| 70586-037 | 2E002 | 20 | 12 | 14.1 |

TABLE 21-continued

Cleavage yield depending upon the temperature at cleavage duration of 12 h

| Number of experiment | Batch of lixisenatide-resin(1-44) | Temperature [° C.] | Duration [h] | Yield [%] |
|---|---|---|---|---|
| 70586-039 | 2E002 | 23 | 12 | 13.0 |
| 70586-045 | 2E002 | 26 | 12 | 14.0 |
| 70586-047 | 2E002 | 30 | 12 | 12.1 |

Results: The yield increases at a cleavage duration of 12 h if reaction temperature is increased. A maximum yield is obtained at 26° C., as described in Example 7.1 for 4 h cleavage. Tests 70586-044 (4 h, 26° C., Example 7) and 70586-045 (12 h, 26° C.) resulted in similar yields (14.8% vs. 14.0%).

7.4 Cleavage Yield Depending Upon the Cleavage Temperature Up to 20° C.

Cleavage from the lixisenatide-resin(1-44) was performed under standard conditions (comparative process, see Table 17) for 4 h.

TABLE 22

Cleavage yield depending upon the cleavage temperature up to 20° C.

| Number of experiment | Batch of lixisenatide-resin(1-44) | Temperature [° C.] | Duration [h] | Yield [%] |
|---|---|---|---|---|
| 71002-028 | 2E002 | 0-5° C. | 21.5 | 6.0 |
| 71002-029 | 2E002 | 8-13° C. | 28 | 8.7 |
| 71002-030 | 2E002 | 8-13° C. | 40.8 | 11.2 |
| 70586-040 | 2E002 | 17° C. | 12 | 10.7 |
| Standard | 2E002 | 20° C. | 4 | 10.3 ± 1.5 |
| 70586-037, 71003-002, 71003-004 | 2E002 | 2° C. | 12 | 13.1 ± 0.9 |

Results: The cleavage at a temperature below 20° C. requires longer cleavage durations, as expected, to reach the yield obtained by cleavage at 20° C. for 4 h (standard conditions, comparative process, Table 17).

7.5 Modified Cleavage Cocktail

The standard process uses a cleavage cocktail containing five components: phenol, thioanisole, 1,2-ethandithiole, water and TFA. Subject of the example are simplified cleavage cocktails, omitting one to three of thioanisole, phenol and water. The yield of lixisenatide cleavage from lixisenatide-resin(1-44) is determined. The "no modification" cocktail is described in Table 17, "Comparative process".

TABLE 23

Modified cleavage cocktail

| Number of experiment | Batch of lixisenatide-resin(1-44) | Modification of cleavage composition | Yield [%] |
|---|---|---|---|
| Standard | 2E002 | no modification | 10.3 ± 1.5 |
| 71002-010 | 2E002 | without thioanisole | 10.7 |
| 71002-009 | 2E002 | without phenol | 12.1 |
| 71002-006 | 2E002 | without water | 13.2 |
| 71002-008 | 2E002 | without phenol and water | 13.3 |
| 71003-008 | 2E002 | water content is reduced to 2.5% w/w | 13.3 |

TABLE 23-continued

Modified cleavage cocktail

| Number of experiment | Batch of lixisenatide-resin(1-44) | Modification of cleavage composition | Yield [%] |
|---|---|---|---|
| 71002-042 | 2E002 | without thioanisole, phenol and water, i.e. only TFA and 1,2-ethanedithiol | 12.7 |

Results: Omission of one or more components results in an increased yield, except test 71002-010 (omission of thioanisole).

A simplified cleavage mixture (cleavage cocktail) has several advantages:

(a) simplification of analytics and quality control,
(b) reduced costs,
(c) facilitated handling in the production process.

7.6 TFA and 1,2-Ethanedithiol Content in the Cleavage Cocktail

Starting from test 71002-042, the influence of the TFA: 1,2-ethanedithiol ratio upon cleavage yield was investigated:

TABLE 24

Different TFA and 1,2-ethanedithiol ratio in the cleavage cocktail

| Number of Experiment | Batch of Lixisenatide-resin (1-44) | Volume in mL of TFA and 1,2-ethanedithiol per g „peptide on resin" | Yield [%] |
|---|---|---|---|
| Standard | 2E002 | | 10.3 ± 1.5 |
| 71002-045 | 2E002 | 8:2 | 6.5 |
| 71002-043 | 2E002 | 9:1 | 9.3 |
| 71002-044 | 2E002 | 9:0.5 | 11.0 |
| 71002-042 | 2E002 | 8.25:0.25 | 12.7 |
| Standard | 2B008 | | 13.4 ± 1.4 |
| 71002-046 | 2B008 | 8.25:0.25 | 15.6 |
| 71002-047 | 2B008 | 8.25:0.25 | 14.3 |

Results: An increase in the 1,2-ethanedithiol content results in a significant decrease of lixisenatide yield. The TFA:1,2-ethanedithiol ratio of 8.25:0.25 was found to be the ratio with largest yield (batch 2E002). This finding was confirmed by to experiments using batch 2B008.

7.7 Volume of the Cleavage Cocktail

The influence of volume (and thus concentration) of the cleavage cocktail was investigated

TABLE 25

Cleavage yield, depending upon volume of the cleavage cocktail.

| Number of Experiment | Batch of Lixisenatide-resin (1-44) | Reduction of volume [%] | Yield [%] |
|---|---|---|---|
| Standard | 2E002 | 0% | 10.3 ± 1.5 |
| 71002-026 | 2E002 | −10% | 13.3 |
| 71002-040 | 2E002 | −15% | 10.3 |
| 71002-025 | 2E002 | −25% | 11.0 |
| 70609-069 | 2E002 | −30% | 10.5 |
| 71002-031 | 2E002 | −50% | 7.9 |

Results: The reduction of up to 30% has no influence upon cleavage yield. Larger volume reductions lead to a decreased yield.

7.8 Swelling of the "Peptide on Resin" with a Co-Solvent (Toluol or $CH_2Cl_2$) Before Cleavage The rationale behind this experiment is the finding that cleavage of lixisenatide from the resin may result in an increase in temperature of up to 5-8° C., which may lead to formation of undesired by-products and potentially has a negative impact upon stability and thus the cleavage yield. Swelling of the "peptide on resin" in an organic solvent may reduce the exotherm and thus may increase the yield.

TABLE 26

Cleavage yield, depending upon the presence of a co-solvent.

| Number of Experiment | Batch of Lixisenatide-resin (1-44) | Swelling with organic solvent | Duration [h] | Increase of temperature [° C.] | Yield [%] |
|---|---|---|---|---|---|
| Standard | 2E002 | without | | 5-8° C. | 10.3 ± 1.5 |
| 71002-016 | 2E002 | 30 ml toluol* | 4 h | 1-2° C. | 9.8 |
| 71002-019 | 2E002 | 30 ml toluol | 6 h | 1-2° C. | 6.1 |
| 71002-021 | 2E002 | 30 ml toluol | 17 h | 1-2° C. | 9.3 |
| 71002-017 | 2E002 | 50 ml toluol | 28 h | 1-2° C. | 4.7 |
| 71002-024 | 2E002 | 30 ml $CH_2Cl_2$ | 24 h | 1-2° C. | 7.3 |

*The total volume of TFA and toluol/$CH_2Cl_2$ is kept constant.

Results: Swelling with an organic co-solvent does not increase the cleavage yield.

7.9 Concentration in the Presence of a Co-Solvent

The presence of a co-solvent, having a higher boiling point than TFA, and in which lixisenatide is insoluble, may increase the yield after cleavage from the resin, because during distillation of TFA from the filtrate, the presence of the co-solvent may lead to precipitation of lixisenatide, and therefore can prevent the degradation of lixisenatide during cleavage in King's cocktail.

TABLE 27

Cleavage yield, depending upon the presence of a co-solvent during TFA distillation.

| Number of Experiment | Batch of lixisenatide-resin(1-44) | Solvent | Yield [%] |
|---|---|---|---|
| Standard | 2E002 | Ohne | 10.3 ± 1.5 |
| 71002-004 | 2E002 | Toluol | 12.0 |
| 71002-014 | 2E002 | n-Heptan | 11.1 |

Results: The presence of toluol in the distillation of the filtrate after cleavage of lixisenatide from the resin leads to a slightly increased yield.

7.10 Optimized Cleavage Procedure of the Invention

Based upon the above-described results obtained in this Example, optimized cleavage conditions as follows were selected and tested:

(a) reaction temperature of 26° C.,
(b) cleavage cocktail consists of TFA and 1,2-ethanedithiol. The cocktail contained about 97% of TFA and about 3% of 1,2-ethanedithiol. An amount of 8.25 ml/g "peptide on resin" of TFA and 0.25 ml/g "peptide on resin" of 1,2-ethanedithiol was used.

The cleavage yield of this cocktail, compared with the standard comparative cocktail, was tested in batches 2E002 and 2B008.

TABLE 28

Optimized cleavage procedure of the invention

| Number of experiment | Batch of Lixisenatide-resin (1-44) | Modification of cleavage composition | Yield [%] |
|---|---|---|---|
| Standard | 2E002 | no modification | 10.3 ± 1.5 |

TABLE 28-continued

Optimized cleavage procedure of the invention

| Number of experiment | Batch of Lixisenatide-resin (1-44) | Modification of cleavage composition | Yield [%] |
|---|---|---|---|
| 70586-051 | 2E002 | 26° C., only TFA and EDT | 14.9 |
| 71001-012 | 2E002 | 26° C., only TFA and EDT | 15.8 |
| Mean ± standard deviation | | | 15.4 ± 0.6 |
| Standard | 2B008 | no modification | 13.4 ± 1.4 |
| 70586-051 | 2B008 | 26° C., only TFA and EDT | 18.5 |
| 71001-013 | 2B008 | 26° C., only TFA and EDT | 19.7 |
| Mean ± standard deviation | | | 19.4 ± 0.4 |

Results: In both batches, the yield increased by about 5%, indicating a significant improvement of the peptide cleavage from the solid phase by the method of the invention.

7.11 Second (Subsequent) Cleavage

After the cleavage, using the comparative cocktail (King's cocktail) or the cleavage cocktail of the invention, a second (subsequent) cleavage, was performed (see Table 17).

The first cleavage was performed, a filtrate was obtained. TFA was added to the TFA-wet resin. After 1 h stirring, the resin was filtrated. The filtrates were combined and concentrated.

The effect of the second, subsequent cleavage upon lixisenatide yield was investigated.

TABLE 29

Influence of a second (subsequent) cleavage of lixisenatide yield.

| Number of experiment | Batch of Lixisenatide-resin (1-44) | Modification of cleavage composition | Subsequent cleavage (TFA only) | Yield [%] |
|---|---|---|---|---|
| Standard | 2B008 | 26° C., only TFA and EDT | yes | 13.4 ± 1.4 |

TABLE 29-continued

Influence of a second (subsequent) cleavage of lixisenatide yield.

| Number of experiment | Batch of Lixisenatide-resin (1-44) | Modification of cleavage composition | Subsequent cleavage (TFA only) | Yield [%] |
|---|---|---|---|---|
| 70586-051 | 2B008 | 26° C., only TFA and EDT | yes | 18.5 |
| 71001-013 | 2B008 | 26° C., only TFA and EDT | yes | 19.7 |
| Mean ± standard deviation | | | | 19.1 ± 0.4 |
| 70001-018 | 2B008 | 26° C., only TFA and EDT | no | 17.9 |
| 70001-019 | 2B008 | 26° C., only TFA and EDT | no | 18.1 |
| 70609-078 | 2B008 | 26° C., only TFA and EDT | no | 18.1 |
| 70001-020 | 2B008 | 26° C., only TFA and EDT | no | 20.1 |
| Mean ± standard deviation | | | | 18.4 ± 1.1 |

EDT: 1,2-ethanedithiol.

Results: Subsequent cleavage results in an increase of the yield of only about 0.7%. This increase is associated with a significant increase in costs for starting materials (TFA), and additional efforts to remove the TFA from the peptide preparation. It must be considered that by combination of the filtrates of the first and second cleavage step, the amount of TFA significantly increases.

It is concluded that in view of the small increase in yield, omission of the second cleavage leads to a cost reduction, and handling during the production process is facilitated. The amounts of TFA are reduced, so that removal of TFA is facilitated.

7.12 Analytics

Two batches, 71001-016 (comparative batch, cleavage with King's cocktail according to the standard method), and 71001-013 (lixisenatide cleavage according to the invention) were prepared.

TABLE 30 analytics

| | Output weight [g] | Content against external standard [%] | Purity [Fl.-%] | Yield [%] |
|---|---|---|---|---|
| 71001-016 (comparative) | 3.41 | 23.0 | 35.6 | 14.2 |
| 71001-013 (invention) | 5.20 | 20.5 | 35.9 | 19.7 |

Results: The batches showed almost identical purity. The content in the batch produced according to the invention is slightly decreased. In the batch of the invention, the output weight is increased, resulting in an increased yield.

7.13 Summary

The cleavage method of the invention has the following advantages:

(a) increase of lixisenatide yield by about 5%, resulting in a cost reduction and an increase of production capacity.

(b) only two components are present in the cleavage cocktail (in view of five components in the comparative King's cocktail), thus analytic quality control is improved and costs are reduced, (c) omission of the second cleavage leads to a cost reduction, and handling during the production process is facilitated. The amounts of TFA are reduced, so that removal of TFA is facilitated.

The following aspects are also subject of the invention:

1. A method for the cleavage of a solid phase-bound polypeptide from the solid phase, the method comprising contacting the solid phase, to which the polypeptide is bound, with a composition consisting essentially of trifluoroacetic acid and 1,2-ethanedithiol, at a temperature in the range of about 23° C. to about 29° C.

2. The method of item 1, wherein the solid phase comprises a Rink amide resin.

3. The method of item 1 or 2, wherein the polypeptide is bound to the Rink amide resin by a linker.

4. The method of any one of the preceding items, wherein the composition comprises trifluoroacetic acid in an amount of about 95 to about 99% v/v.

5. The method of any one of the preceding items, wherein the composition comprises 1,2-ethanedithiol in an amount of about 1 to about 5% v/v.

6. The method of any one of the preceding items, wherein the composition essentially consists of trifluoroacetic acid in an amount of about 97% v/v, and 1,2-ethanedithiol in an amount of about 3% v/v.

7. The method of any one of the preceding items, wherein the composition is contacted with the solid phase to which the polypeptide is bound, at a temperature of about 25° C. to about 27° C., or at a temperature of about 26° C. to about 29° C.

8. The method of any one of the preceding items, wherein the composition is contacted with the solid phase to which the polypeptide is bound, at a temperature of about 26° C.

9. The method of any one of the preceding items, wherein the composition is contacted with the solid phase to which the polypeptide is bound for 1 to 8 h.

10. The method of any one of the items 1 to 9, wherein the composition is contacted with the solid phase to which the polypeptide is bound for 4 to 8 h.

11. The method of any one of the items 1 to 9, wherein the composition is contacted with the solid phase to which the polypeptide is bound for 3 to 5 h.

12. The method of any one of the preceding items, wherein the composition is contacted with the solid phase to which the polypeptide is bound for about 4 h.

13. The method of any one of the preceding items, wherein the polypeptide is selected from GLP-1, analogs and derivatives thereof, exendin-3, analogs and derivatives thereof, and exendin-4, analogs and derivatives thereof.

14. The method of item 13, wherein the polypeptide is selected from exendin-4 and lixisenatide.

15. The method of item 13, wherein the polypeptide is selected from albiglutide, dulaglutide and semaglutide.

16. The method of item 13 or 14, wherein the polypeptide is lixisenatide.

17. A method for the solid-phase synthesis of a polypeptide comprising a pre-determined amino acid sequence, said method comprising:

(a) coupling an amino acid building block, comprising an unprotected C-terminal carboxyl group and a protected N-terminal amino group, C-terminally to a solid phase, such as a Rink amide resin, (b) de-protecting the N-terminal amino group of the amino acid building block, (c) coupling an amino acid building block, comprising an unprotected C-terminal carboxyl group and a protected N-terminal amino group, C-terminally to the unprotected N-terminal amino of step (b), (d) optionally repeating steps (b) and (c), and (e) cleaving the polypeptide from the solid phase by the method of any one of the items 1 to 16.

18. The method of item 17, wherein the polypeptide is selected from GLP-1, analogs and derivatives thereof, exendin-3, analogs and derivatives thereof, and exendin-4, analogs and derivatives thereof.

19. The method of item 17 or 18, wherein the polypeptide is selected from exendin-4 and lixisenatide.

20. The method of item 17 or 18, wherein the polypeptide is selected albiglutide, dulaglutide and semaglutide.

21. The method of any one of the items 17 to 19, wherein the polypeptide is lixisenatide.

22. Composition, consisting essentially of trifluoroacetic acid and 1,2-ethanedithiol, wherein the composition comprises trifluoroacetic acid in an amount of 95 to 99% v/v, and 1,2-ethanedithiol in an amount of 1 to 5% v/v.

23. Composition of item 22, essentially consisting of trifluoroacetic acid in an amount of about 97% v/v, and 1,2-ethanedithiol in an amount of about 3% v/v.

24. Use of the composition of item 22 or 23 in a solid-phase synthesis of a polypeptide.

25. The use of item 24, wherein the composition is used to cleave the polypeptide from the solid phase.

26. The use of item 24 or 25, wherein the polypeptide is selected from GLP-1, analogs and derivatives thereof, exendin-3, analogs and derivatives thereof, and exendin-4, analogs and derivatives thereof.

27. The use of any one of the items 24 to 26, wherein the polypeptide is selected from exendin-4, lixisenatide, albiglutide, dulaglutide and semaglutide.

28. The use of any one of the items 24 to 27, wherein the polypeptide is lixisenatide.

The invention claimed is:

1. A method for cleavage of a solid phase-bound polypeptide from a solid phase, the method comprising contacting the solid phase to which the polypeptide is bound, with a composition consisting essentially of trifluoroacetic acid and 1,2-ethanedithiol,
wherein percentages of the trifluoroacetic acid and the 1,2-ethanedithiol in the composition are 100% together, including impurities, which may be present in the trifluoroacetic acid and 1,2-ethanedithiol,
wherein a reaction is at a temperature of 25° C. to 27° C., and
wherein the polypeptide is selected from GLP-1, analogs and derivatives thereof, exendin-3, analogs and derivatives thereof, and exendin-4, analogs and derivatives thereof.

2. The method of claim 1, wherein the solid phase comprises a Rink amide resin.

3. The method of claim 2, wherein the polypeptide is bound to the Rink amide resin by a linker.

4. The method of claim 1, wherein the composition comprises trifluoroacetic acid in an amount of 95 to 99% v/v and 1,2-ethanedithiol in an amount of 1 to 5% v/v.

5. The method of claim 1, wherein the composition consists essentially of trifluoroacetic acid in an amount of 97% v/v, and 1,2-ethanedithiol in an amount of 3% v/v.

6. The method of claim 1, wherein the solid phase to which the polypeptide is bound is contacted with the composition at a temperature of 26° C. to 27° C.

7. The method of claim 6, wherein the solid phase to which the polypeptide is bound is contacted with the composition at a temperature of 26° C.

8. The method of claim 1, wherein the solid phase to which the polypeptide is bound is contacted with the composition for 1 to 8 h.

9. The method of claim 8, wherein the solid phase to which the polypeptide is bound is contacted with the composition for 3 to 5 h.

10. The method of claim 1, wherein the polypeptide is selected from exendin-4, lixisenatide, albiglutide, dulaglutide and semaglutide.

11. The method of claim 1, wherein the cleavage of the solid phase-bound polypeptide is a step in a method of a solid-phase synthesis of the polypeptide.

12. A method for the solid-phase synthesis of a polypeptide comprising a pre-determined amino acid sequence, said method comprising:

(a) coupling an amino acid building block comprising an unprotected C-terminal carboxyl group and a protected N-terminal amino group, C-terminally to a solid phase,
(b) de-protecting the N-terminal amino group of the amino acid building block,
(c) coupling an amino acid building block, comprising an unprotected C-terminal carboxyl group and a protected N-terminal amino group, C-terminally to the unprotected N-terminal amino of step (b),
(d) optionally repeating steps (b) and (c), and
(e) cleaving the polypeptide from the solid phase by contacting the solid phase to which the polypeptide is bound with a composition consisting essentially of trifluoroacetic acid and 1,2-ethanedithiol at a temperature of 25° C. to 27° C.,
wherein percentages of the trifluoroacetic acid and the 1,2-ethanedithiol in the composition are 100% together, including impurities which may be present in the trifluoroacetic acid and 1,2-ethanedithiol, and
wherein the polypeptide is selected from GLP-1, analogs and derivatives thereof, exendin-3, analogs and derivatives thereof, and exendin-4, analogs and derivatives thereof.

13. The method of claim 12, wherein the polypeptide is selected from exendin-4, lixisenatide, albiglutide, dulaglutide and semaglutide.

14. The method of claim 12, wherein the solid phase is a Rink amide resin.

15. A method for cleavage of a solid phase-bound polypeptide from a solid phase, the method comprising contacting the solid phase to which the polypeptide is bound, with a composition consisting essentially of trifluoroacetic acid in an amount of 97% v/v and 1,2-ethanedithiol in an amount of 3% v/v,
wherein percentages of the trifluoroacetic acid and the 1,2-ethanedithiol in the composition are 100% together, including impurities which may be present in the trifluoroacetic acid and 1,2-ethanedithiol,
wherein a reaction temperature is above room temperature, and
wherein the polypeptide is selected from GLP-1, analogs and derivatives thereof, exendin-3, analogs and derivatives thereof, and exendin-4, analogs and derivatives thereof.

* * * * *

```
                              SEQUENCE LISTING

<160> NUMBER OF SEQ ID NOS: 4

<210> SEQ ID NO 1
<211> LENGTH: 44
<212> TYPE: PRT
<213> ORGANISM: Artificial Sequence
<220> FEATURE:
<223> OTHER INFORMATION: lixisenatide

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 2
<211> LENGTH: 39
<212> TYPE: PRT
<213> ORGANISM: Heloderma suspectum
<220> FEATURE:
<223> OTHER INFORMATION: exendin-4

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Heloderma horridum
<220> FEATURE:
<223> OTHER INFORMATION: exendin-3

<400> SEQUENCE: 3

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30
```

```
Ser Gly Ala Pro Pro Pro Ser
        35

<210> SEQ ID NO 4
<211> LENGTH: 30
<212> TYPE: PRT
<213> ORGANISM: human
<220> FEATURE:
<223> OTHER INFORMATION: GLP-1(7-36)

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30
```